United States Patent
Shimada et al.

(10) Patent No.: US 6,524,761 B2
(45) Date of Patent: Feb. 25, 2003

(54) MIXTURE OF TITANYLTETRAAZAPORPHYRIN COMPOUNDS AND ELECTROPHOTOGRAPHIC PHOTOCONDUCTOR USING THE SAME

(75) Inventors: Tomoyuki Shimada, Shizuoka (JP); Masayuki Shoshi, Shizuoka (JP); Kaoru Tadokoro, Kanagawa (JP); Chiaki Tanaka, Shizuoka (JP); Michihiko Namba, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 09/904,896

(22) Filed: Jul. 16, 2001

(65) Prior Publication Data

US 2002/0007056 A1 Jan. 17, 2002

Related U.S. Application Data

(62) Division of application No. 09/441,748, filed on Nov. 17, 1999.

(30) Foreign Application Priority Data

Nov. 18, 1998 (JP) .............................................. 10-328248

(51) Int. Cl.⁷ ................................................. G03G 5/06
(52) U.S. Cl. ............................. 430/58; 430/78; 430/135
(58) Field of Search ............................. 430/78, 58, 135

(56) References Cited

U.S. PATENT DOCUMENTS

| | | | | |
|---|---|---|---|---|
| 4,882,427 A | * | 11/1989 | Enokida et al. ............. | 540/141 |
| 5,112,711 A | * | 5/1992 | Nguyen et al. ............... | 430/58 |
| 5,238,764 A | * | 8/1993 | Molaire et al. ............... | 430/58 |
| 5,773,181 A | * | 6/1998 | Molaire et al. ............... | 430/78 |

FOREIGN PATENT DOCUMENTS

DE 197 38 822 * 3/1999

OTHER PUBLICATIONS

Kuznetsova et al.; Chemical Abstract 1996:215471.
Streitwieser et al.; Introduction to Organic Chemistry, Second Edition, MacMillan, New York, 1981, pp. 544–545.

* cited by examiner

Primary Examiner—Richard L. Raymond
Assistant Examiner—Kahsay Habte
(74) Attorney, Agent, or Firm—Oblon, Spivak, McClelland, Maier & Neustadt, P.C.

(57) ABSTRACT

A mixture is made of a plurality of different titanyltetraazaporphyrin compounds, each of which is represented by formula (1):

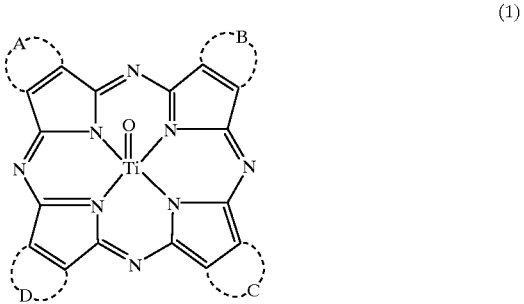

wherein A, B, C and D are each independently an unsubstituted or substituted benzene ring or pyridine ring, a substituent thereof being selected from the group consisting of nitro group, cyano group, a halogen atom, an alkyl group having 1 to 8 carbon atoms, an alkoxyl group having 1 to 8 carbon atoms, and an aryl group. The above-mentioned mixture is contained in a photoconductive layer of an electrophotographic photoconductor as a photoconductive material.

9 Claims, 11 Drawing Sheets

MIXTURE OF TITANYLTETRAAZAPORPHYRIN COMPOUNDS AND ELECTROPHOTOGRAPHIC PHOTOCONDUCTOR USING THE SAME

This application is a Division of application Ser. No. 09/441,748 filed on Nov. 17, 1999, now allowed.

BACKGROUND OF THE INVENTION

1. Field of the Invention

The present invention relates to a mixture of a plurality of different titanyltetraazaporphyrin compounds, and an electrophotographic photoconductor comprising a photoconductive layer in which the above-mentioned mixture of the titanyltetraazaporphyrin compounds is contained as the photoconductive material.

2. Discussion of Background

Conventionally, the photoconductive material for use in the electrophotographic process is roughly divided into two groups, that is, an inorganic photoconductive material and an organic photoconductive material. The above-mentioned electrophotographic process is one of the image forming processes, through which the surface of the photoconductor is charged uniformly in the dark to a predetermined polarity, for instance, by corona charge. The uniformly charged photoconductor is exposed to a light image to selectively dissipate the electric charge of the exposed area, so that a latent electrostatic image is formed on the photoconductor. The thus formed latent electrostatic image is developed into a visible image by use of a toner comprising a coloring agent such as a dye or pigment, and a polymeric material. Such an electrophotographic process is called "Carlson process".

The photoconductor employing the organic photoconductive material is advantageous over that employing the inorganic photoconductive material with respect to the degree of freedom in the wave range of the light to be employed, and the film-forming properties, flexibility, transparency, productivity, toxicity, and manufacturing cost of the photoconductor. In light of the above-mentioned advantages, most of the current photoconductors employ the organic photoconductive material.

The photoconductor which is repeatedly operated by the above-mentioned electrophotographic process or the like is required to exhibit excellent electrostatic properties, more specifically, excellent photosensitivity, acceptance potential, retentivity of charge, potential stability, residual potential, and spectral sensitivity.

In recent years, the development of data processing apparatus employing the above-mentioned electrophotographic process is remarkable. In particular, there is a remarkable improvement in the printing quality and the reliability of the digital printer which is capable of recording data by digital recording method, to be more specific, converting the data into digital signals and recording the data using a light. Such a digital recording system is applied not only to the printer, but also to the copying machine. Thus, the digital copying machine is actively developed. It is supposed that the demand for the digital copying machine will further increase in line with the addition of various data processing functions.

The photoconductor designed for the above-mentioned digital recording system is required to have special characteristics which are different from those required for the conventional analogue recording system. For instance, semiconductor laser (LD) or light emitting diode (LED) is widely employed as a light source for the digital recording system because of its compactness, cheapness and high reliability. The wave range of the currently used Lo is within the near infrared region, and the wavelength of the currently used LED is 650 nm or more. Therefore, the electrophotographic photoconductors for use with the above-mentioned digital recording system are required to show sufficient sensitivity in the wavelength range from the visible region to the near infrared region.

In light of the above-mentioned sensitivity, a squarylium dye (Japanese Laid-Open Patent Applications 49-105536 and 58-21416), a triphenylamine trisazo pigment (Japanese Laid-Open Patent Application 61-151659), and a phthalocyanine pigment (Japanese Laid-Open Patent Applications 48-34189 and 57-14874) are proposed as the photoconductive materials for use in the digital recording.

In particular, the phthalocyanine pigment, that is, a titanyltetraazaporphyrin compound, can show absorption and photosensitivity in the relatively long wavelength range. In addition, a variety of phthalocyanine pigments can be obtained according to the kind of central metal or the type of crystalline form. Therefore, research and development of this type of phthalocyanine pigment has been actively conducted to obtain the improved photoconductive material for use with the digital recording.

Examples of the conventional phthalocyanine pigments capable of showing good sensitivity include $\epsilon$-type copper phthalocyanine, X-type metal-free phthalocyanine, t-type metal-free phthalocyanine, vanadyl phthalocyanine, and titanyl phthalocyanine.

To be more specific, titanylphthalocyanine pigments with high sensitivity are proposed in Japanese Laid-Open Patent Applications 64-17066, 3-128973 and 5-98182. Those titanylphthalocyanine pigments exhibit maximum absorption in the wavelength range of 700 to 860 nm, so that they can show remarkably high sensitivity with respect to the semiconductor laser beam. However, when each of the above-mentioned titanylphthalocyanine pigments is employed in the electrophotographic photoconductor, there still remain a lot of practical problems, for example, decline in charging performance due to fatigue, and temperature- and humidity-dependence of the charging characteristics although the sensitivity is sufficient. This is reported in Y. Fujimaki, Proc. IS&Ts 7th International Congress on Advances in Non-Impact Printing Technologies, 1,269 (1991); K. Daimon et al.; J. Imaging Sci. Technol., 40,249 (1996).

Japanese Patent Nos. 2637487 and 2637485 disclose tetraazaporphyrin pigments having a heterocycle such as pyridine or pyrazine. Further, Japanese Patent Publication No. 3-27111 and Japanese Patent No. 2754739 discloses that a mixture of a phthalocyanine pigment and a pyridinoporphyradine pigment is effective as the photoconductive material.

In addition, a mixture of copper-tetraazaporphyrin compounds obtained by allowing pyridine-3,4-dicarboxylic acid to react with phthalic anhydride is disclosed in Japanese Patent Publication No. 3-27111.

Even though those photoconductive materials are employed in the electrophotographic photoconductor, the above-mentioned requirements for the photoconductor are not satisfied. Namely, the sensitivity in the visible light range and the near infrared range, and the charging characteristics are still unsatisfactory, and in particular, the durability of the photoconductor is insufficient when the photoconductor is subjected to repeated electrophotographic operations.

SUMMARY OF THE INVENTION

Accordingly, it is a first object to provide an organic photoconductive material for use in the electrophotographic photoconductor, free of the shortcomings of the conventional photoconductive materials, capable of exhibiting high sensitivity with respect to light from the visible light range to the near infrared range, excellent charging characteristics, and stable electrostatic characteristics in the fatigue properties.

A second object of the present invention is to provide a method of producing the above-mentioned photoconductive material.

A third object of the present invention is to provide an electrophotographic photoconductor employing the above-mentioned photoconductive material.

A fourth object of the present invention is to provide an image forming apparatus comprising the above-mentioned photoconductor.

The first object of the present invention can be achieved by a mixture of a plurality of different titanyltetraazaporphyrin compounds, each of which is represented by formula (1):

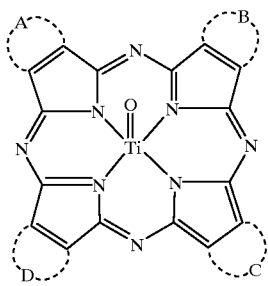

(1)

wherein A, B, C and D are each independently an unsubstituted or substituted benzene ring or pyridine ring, a substituent thereof being selected from the group consisting of nitro group, cyano group, a halogen atom, an alkyl group having 1 to 8 carbon atoms, an alkoxyl group having 1 to 8 carbon atoms, and an aryl group.

It is preferable that the above-mentioned mixture of titanyltetraazaporphyrin compounds exhibit peaks at 576, 577, 579, 579 and 580 when subjected to mass spectrometric analysis.

Further, it is preferable that the above-mentioned mixture comprise (a) a titanyltetraazaporphyrin compound with formula (1) in which A, B, C and D are each an unsubstituted benzene ring, (b) a titanyltetraazaporphyrin compound with formula (1) in which three of A, B, C and D are each an unsubstituted benzene ring and the rest thereof is an unsubstituted pyridine ring, (c) a titanyltetraazaporphyrin compound with formula (1) in which two of A, B, C and D are each an unsubstituted benzene ring and the rest thereof are each an unsubstituted pyridine ring, (d) a titanyltetraazaporphyrin compound with formula (1) in which one of A, B, C or D is an unsubstituted benzene ring, and the rest thereof are each an unsubstituted pyridine ring, and (e) a titanyltetraazaporphyrin compound with formula (1) in which A, B, C and D are each an unsubstituted pyridine ring.

Furthermore, it is preferable that the mixture exhibit at least one of diffraction peaks at 6.9°, 26.2°, 27.2° and 28.5° in terms of a Bragg angle of 2θ±0.2° in an X-ray diffraction spectrum using a Cu-Kα ray with a wavelength of 1.54 Å.

The mixture of titanyltetraazaporphyrin compounds may be produced by allowing phthalonitrile, dicyanopyridine, and a titanium compound to react.

The second object of the present invention can be achieved by a method of producing at least one mixture of a plurality of different titanyltetraazaporphyrin compounds, each of which titanyltetraazaporphyrin compounds is represented by the above-mentioned formula (1), comprising the step of allowing phthalonitrile, dicyanopyridine, and a titanium compound to react.

In the above-mentioned preparation method, at least two of the mixtures which are different may be produced and mixed, each of the different mixtures being produced by mixing the phthalonitrile and the dicyanopyridine at a different mixing ratio.

In the above-mentioned preparation method, a phthalocyanine pigment may be added to the mixture when the phthalonitrile and the dicyanopyridine are mixed.

In addition, it is preferable that the preparation method further comprise the step of subjecting the mixture to crystal modification treatment.

The third object of the present invention can be achieved by an electrophotographic photoconductor which comprises an electroconductive support and a photoconductive layer formed thereon comprising a mixture of a plurality of different titanyltetraazaporphyrin compounds, each of which is represented by the above-mentioned formula (1).

The fourth object of the present invention can be achieved by an image forming apparatus comprising an electrophotographic photoconductor which comprises an electroconductive support and a photoconductive layer formed thereon comprising a mixture of a plurality of different titanyltetraazaporphyrin compounds, each of which is represented by the above-mentioned formula (1).

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
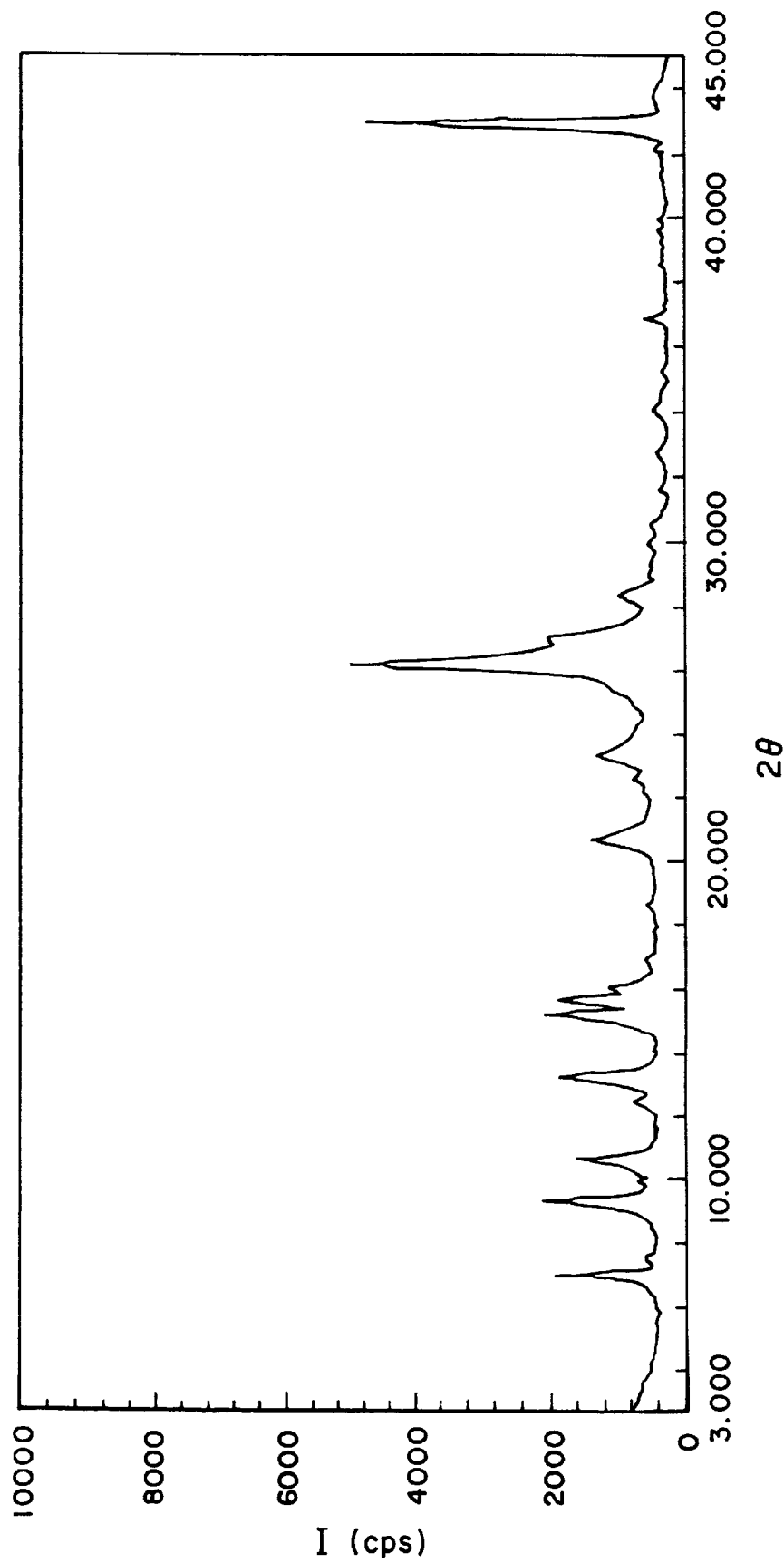
FIG. 1 is an X-ray diffraction spectrum of a mixture (No. 1) of titanyltetraazaporphyrin compounds in the form of a powder obtained in Example 1—1.

In the mixture of a plurality of different titanyltetraazaporphyrin compounds according to the present invention, each titanyltetraazaporphyrin compound is represented by formula (1):

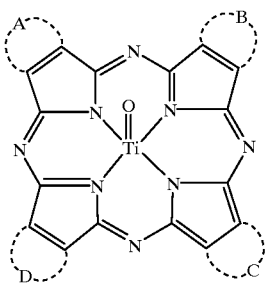

(1)

wherein A, B, C and D are each independently an unsubstituted or substituted benzene ring or pyridine ring, a substituent thereof being selected from the group consisting of cyano group, a halogen atom, an alkyl group having 1 to 8 carbon atoms, an alkoxyl group having 1 to 8 carbon atoms, and an aryl group.

The above-mentioned mixture, which is novel, can be conveniently, reproducibly and surely obtained in high yield according to the preparation method of the present invention.

A plurality of different titanyltetraazaporphyrin compounds in the mixture of the present invention can be confirmed and analyzed, for example, by mass spectrometric analysis. Namely, by observing the fragment peaks of molecular weight, each titanyltetraazaporphyrin compound corresponding to the molecular weight can be identified.

The sensitivity of the electrophotographic photoconductor which contains such a mixture of the titanyltetraazaporphyrin compounds as specified in the present invention becomes better than that of the photoconductor which employs a mixture of tetraazaporphyrin compounds having other center metals than titanium. Understandably therefore, titanium as the center metal is considered to contribute to the improvement of sensitivity. Further, when the electrophotographic photoconductor comprises a mixture of the titanyltetraazaporphyrin compounds according to the present invention, the electrostatic stability of the photoconductor after repeated electrophotographic operations is superior to that of the photoconductor employing the conventional titanyl phthalocyanine pigment. The use of a plurality of titanyltetraazaporphyrin compounds in the form of a mixture is supposed to be beneficial to the electrostatic stability.

In the aforementioned formula (1), A, B, C and D are each a benzene ring which may have a substituent, or a pyridine ring which may have a substituent.

Examples of the substituent for the benzene ring or pyridine ring include nitro group, cyano group, a halogen atom, an alkyl group which may have a substituent, an alkoxyl group which may have a substituent, and an aryl group which may have a substituent.

Specific examples of the above-mentioned halogen atom serving as the substituent are iodine atom, bromine atom, chlorine atom, and fluorine atom.

Specific examples of the above-mentioned alkyl group serving as the substituent include methyl group, ethyl group, n-propyl group, iso-propyl group, tert-butyl group, sec-butyl group, n-butyl group, iso-butyl group, trifluoromethyl group, 2-cyancethyl group, benzyl group, 4-chlorobenzyl group, and 4-methylbenzyl group.

Specific examples of the above-mentioned alkoxyl group serving as the substituent include methoxy group, ethoxy group, n-propoxy group, iso-propoxy group, n-butoxy group, iso-butoxy group, sec-butoxy group, tert-butoxy group, 2-hydroxyethoxy group, 2-cyanoethoxy group, benzyloxy group, 4-methylbenzyloxy group, and trifluoromethoxy group.

Specific examples of the above-mentioned aryl group serving as the substituent include phenyl group, naphthyl group, biphenylyl group, terphenylyl group, pyrenyl group, fluorenyl group, 9,9-dimethyl-2-fluorenyl group, azulenyl group, anthryl group, triphenylenyl group, chrysenyl group, fluorenylidenephenyl group, 5H-dibenzo[a,d] cycloheptenylidenephenyl group, thienyl group, benzothienyl group, furyl group, benzofuranyl group, carbazolyl group, pyridyl group, pyridinyl group, pyrrolidyl group and oxazolyl group.

The aryl group may have a substituent such as the same alkyl group, alkoxyl group and halogen atom as previously mentioned. Further, the aryl group may form a fused ring together with the ring of A, B, C or D.

The mixture of titanyltetraazaporphyrin compounds, each of which is represented by the above-mentioned formula (1), can be obtained, for example, by allowing a mixture of phthalonitrile of formula (2) and dicyanopyridine of formula (3) or (4), which are shown below, to react with a titanium compound such as titanium tetrachloride or tetra-n-butyl o-titanate. This reaction may be carried out with no solvent, or in a solvent such as α-chloronaphthalene, dichlorobenzene, trichlorobenzene, pentanol, octanol, benzyl alcohol, N,N-dimethylformamide, N-methylpyrrolidone, quinoline, benzene, toluene, xylene, mesitylene, nitrobenzene or dioxane.

Further, this reaction may be carried out in the presence of urea, formamide, acetcamide, benzamide, 1,8-diazabicyclo[5, 4,0]-7-undecene (DBU), or ammonia.

The reaction temperature is commonly set wihin the range from room temperature to 300° C., preferably 100 to 250° C.

For convenience, both the phthalonitrile of formula (2) and the dicyanopyridine of formula (3) or (4) have no substituent. Both may have such a substituent as mentioned above.

The phthalonitrile as the starting material, represented by formula (2), may be replaced by the compounds of formulas (5) to (7), while the dicyanopyridine as the starting material, represented by formula (3) or (4), may be replaced by the compounds of formulas (8) to (13) In this case, the mixture of the titanyltetraazaporphyrin compounds of formula (1) can be produced in a similar manner as mentioned above.

(2)
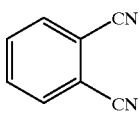

(3)
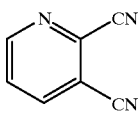

(4)
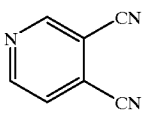

(5)
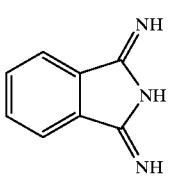

(6)
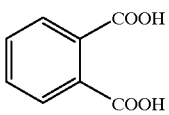

(7)
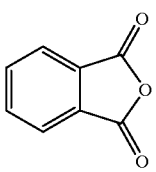

(8)
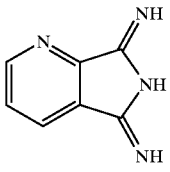

(9)
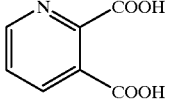

(10)
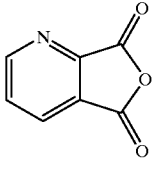

(11)
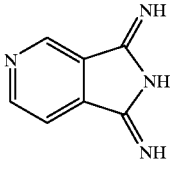

-continued

(12)
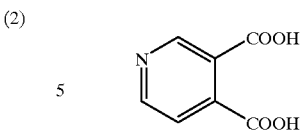

(13)
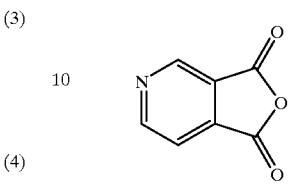

In the synthesis of the mixture of the titanyltetraazaporphyrin compounds, it is preferable that the molar ratio of the phthalonitrile of formula (2) to the dicyanopyridine of formula (3) or (4) be in the range of (1:99999) to (99999:1), more preferably in the range of (1:1) to (399:1). When the molar ratio of the phthalonitrile is less than the above-mentioned lower limit, the charging characteristics and the sensitivity of the obtained photoconductor tend to decrease. When the molar ratio of the dicyanopyridine is less than the above-mentioned lower limit, the decrease of chargeability due to fatigue becomes large after the repeated charging and light exposure.

In response to the requirements for the photoconductor, two or more different mixtures of the titanyltetraazaporphyrin compounds may be produced and mixed, each of the different mixtures being produced by mixing the phthalonitrile and the dicyanopyridine at a different mixing ratio.

Furthermore, a phthalocyanine pigment may be added to the mixture when the phthalonitrile and the dicyanopyridine are mixed.

Examples of the phthalocyanine pigment for use in the present invention include copper phthalocyanine, metal-free phthalocyanine, aluminum phthalocyanine, magnesium phthalocyanine, chlorogallium phthalocyanine, hydroxygallium phthalocyanine, vanadyl phthalocyanine, titanyl phthalocyanine, chloroindium phthalocyanine, hydroxyindium phthalocyanine, zinc phthalocyanine, iron phthalocyanine, and cobalt phthalocyanine.

It is preferable that the mixture of a plurality of different titanyltetraazaporphyrin compounds of the present invention be in a crystalline state, in particular, be in such a specific crystalline form that exhibits at least a diffraction peak at 6.9°, 26.2°, 27.2° or 28.5° in terms of a Bragg angle $2\theta \pm 0.2°$ in an X-ray diffraction spectrum using a Cu-Kα ray ($\lambda=1.54$ Å).

The above-mentioned preparation method of the mixture of titanyltetraazaporphyrin compounds makes it possible to obtain the mixture in a crystalline state. Further, a desired crystalline form may be obtained by subjecting the mixture to crystal modification treatment.

To be more specific, acid treatment, solvent treatment, mechanical treatment, and heating treatment are available as the crystal modification treatment methods of a mixture of the titanyltetraazaporphyrin compounds.

The acid treatment is carried out in such a manner that the mixture of titanyltetraazaporphyrin compounds is first dissolved in an acid such as trichloroacetic acid or trifluoroacetic acid at a temperature ranging from 0° C. to room temperature. The thus prepared solution is added dropwise to ice-cold water or an organic solvent in which the mixture of the titanyltetraazaporphyrin compounds is slightly soluble to precipitate the crystals of the mixture. The precipitated crystals are collected, for example, by filtration.

In the treatment using a solvent, the mixture of the titanyltetraazaporphyrin compounds is suspended in a solvent with stirring at room temperature or under the application of heat.

The previously mentioned mechanical treatment means milling treatment by use of, for example, automatic mortar, planetary mill, ball mill, oscillating ball mill, kneader, attritor, or sand mill. The milling treatment is performed at room temperature or under the application of heat, using milling media such as glass beads, steel beads, alumina balls, PSZ balls, YTZ balls, salt, and Glauber's salt. The mixture of the titanyltetraazaporphyrin compounds may be subjected to milling using the above-mentioned media in a solvent.

The heating treatment is carried out in combination with the above-mentioned acid treatment, solvent treatment, or mechanical treatment. In addition, the crystals of the mixture of the titanyltetraazaporphyrin compounds may be directly heated at a temperature higher than the crystalline transition temperature using an electric furnace in the atmosphere or in the presence of an inert gas.

Specific examples of the solvent used in the above-mentioned treatment include aromatic solvents such as benzene, toluene, dichlorobenzene, and nitrobenzene; alcohols such as methanol, ethanol, and benzyl alcohol; ketones such as acetone, cyclohexanone, and methyl ethyl ketone; ethers such as n-butyl ether, ethylene glycol n-butyl ether, and tetrahydrofuran; amines such as N,N-dimethylformamide, and N-methylpyrrolidone; basic solvents such as quinoline and pyridine; dimethyl sulfoxide; and water.

A plurality of different titanyltetraazaporphyrin compounds in the mixture can be confirmed and analyzed, for example, by mass spectrometric analysis. Namely, by confirming the presence of a fragment peak corresponding to the molecular weight of each titanyltetraazaporphyrin compound, the titanyltetraazaporphyrin compound can be identified.

An electrophotographic photoconductor of a single-layered type or a layered type (function-separating type) can be fabricated, using as the photoconductive material the mixture of titanyltetraazaporphyrin compounds according to the present invention alone, or in combination with a charge transport material.

To fabricate the electrophotographic photoconductor of a single-layered type, a photoconductive layer is provided on an electroconductive support in such a manner that a mixture of titanyltetraazaporphyrin compounds is singly dispersed in a binder resin or together with a charge transport material, and the thus prepared dispersion is coated on the support.

In the case where the electrophotographic photoconductor of a layered type (function-separating type) is fabricated, a charge generation layer comprising a mixture of titanyltetraazaporphyrin compounds is provided on an electroconductive support, and a charge transport layer comprising a charge transport material is overlaid on the charge generation layer. The above-mentioned overlaying order of the charge generation layer, and the charge transport layer may be reversed.

The electrophotographic photoconductor of the present invention may further comprise an intermediate layer which is provided between the electroconductive support and the photoconductive layer in order to improve the adhesion between the support and the photoconductive layer, and enhance the charge blocking characteristics.

Furthermore, a protective layer may be provided on the photoconductive layer to improve the wear resistance and the mechanical durability of the photoconductor.

To form the photoconductive layer in which a mixture of titanyltetraazaporphyrin compounds is dispersed, the mixture of titanyltetraazaporphyrin compounds, and a binder resin optionally added thereto, are dispersed or dissolved in an appropriate solvent, using a ball mill, ultrasonic wave, or a homomixer. Then, the above prepared coating liquid may be coated on the electroconductive support by dip coating, blade coating or spray coating.

To upgrade the dispersibility of the mixture of titanyltetraazaporphyrin compounds in the photoconductive layer, it is preferable that the average particle size of the mixture of titanyltetraazaporphyrin compounds be 2 $\mu$m or less, more preferably 1 $\mu$m or less. Further, the lower limit of the average particle size may be set at 0.01 $\mu$m so as to inhibit the aggregation of fine particles. Thus, the increase of the resistivity of the photoconductive layer can be prevented, and the deterioration of sensitivity and durability due to the increase of defective crystallites can be prevented in the repeated use.

Specific examples of the solvent which is used to prepare a dispersion or solution for the formation of the photoconductive layer include N,N-dimethylformamide, toluene, xylene, monochlorobenzene, 1,2-dichloroethane, 1,1,1-trichloroethane, dichloromethane, 1,1,2-trichloroethane, trichlorcethylene, tetrahydrofuran, methyl ethyl ketone, methyl isobutyl ketone, cyclohexanone, ethyl acetate, and butyl acetate.

Any binder resin that has good electrically insulating properties and conventionally used in the preparation of the electrophotographic photoconductor can be employed for the formation of the photoconductive layer in the present invention.

Specific examples of such a binder resin include addition polymerization-type resins, polyaddition-type resins and polycondensation-type resins such as polyethylene, polyvinyl butyral, polyvinyl formal, polystyrene resin, phenoxy resin, polypropylene, acrylic resin, methacrylic resin, vinyl chloride resin, vinyl acetate resin, epoxy resin, polyurethane resin, phenolic resin, polyester resin, alkyd resin, polycarbonate resin, polyamide resin, silicone resin and melamine resin; copolymer resins comprising as the repeat units two or more monomers for use in the above-mentioned resins, for example, electrically insulating resins such as vinyl chloride-vinyl acetate copolymer resin, styrene-acrylic copolymer resin, and vinyl chloride-vinyl acetate-maleic anhydride copolymer resin; and a polymeric organic semiconductor such as poly-N-vinylcarbazole. Those binder resins may be used alone or in combination.

The mixture of titanyltetraazaporphyrin compounds according to the present invention may be used in combination with the following pigments: organic pigments, for example, azo pigments such as C.I. Pigment Blue 25 (C.I. 21180), C.I. Pigment Red 41 (C.I. 21200), C.I. Acid Red 52 (C.I. 45100), C.I. Basic Red 3 (C.I. 45210), an azo pigment having a carbazole skeleton (Japanese Laid-Open Patent Application 53-95033), an azo pigment having a distyryl benzene skeleton (Japanese Laid-Open Patent Application 53-133445), an azo pigment having a triphenylamine skeleton (Japanese Laid-Open Patent Application S3-132347), an azo pigment having a dibenzothiophene skeleton (Japanese Laid-Open Patent Application 54-21728), an azo pigment having an oxadiazole skeleton (Japanese Laid-Open Patent Application 54-12742), an azo pigment having a fluorenone skeleton (Japanese Laid-Open Patent Application 54-22834), an azo pigment having a bisstilbene skeleton (Japanese Laid-Open Patent Application 54-17733), an azo pigment having a distyryl oxadiazole skeleton (Japanese Laid-Open Patent Application 54-2129), and an azo pigment having a distyryl carbazole skeleton (Japanese Laid-Open Patent Application 54-14967); phthalocyanine pigments such as C.I. Pigment Blue 16 (C.I. 74100) and titanyl phthalocyanine; indigo pigments such as C.I. Vat Brown 5 (C.I. 73410) and C.I. Vat Dye (C.I. 73030); and perylene pigments such as Algol Scarlet B and Indanthrene Scarlet R (made by Bayer Co., Ltd.). Two or more organic pigments mentioned above may be used in combination with the mixture of titanyltetraazaporphyrin compounds of formula (1).

In the layered photoconductor in which the charge generation layer and the charge transport layer are successively overlaid on the electroconductive support in this order, it is preferable that the amount of the mixture of titanyltetraazaporphyrin compounds in the charge generation layer be in the range of 20 to 900 wt % of the entire weight of the binder resin for use in the charge generation layer. The thickness of the above-mentioned charge generation layer is preferably in the range of 0.01 to 5 μm. Further, in this case, it is preferable that the amount of the charge transport material in the charge transport layer be in the range of 20 to 200 wt % of the entire weight of the binder resin for use in the charge transport layer. The thickness of the charge transport layer is preferably in the range of 5 to 100 μm. The charge transport layer may be formed using a high-molecular weight charge transport material alone.

Further, in such a case, the addition of the charge transport material to the charge generation layer is effective for reducing the residual potential and improving the photosensitivity. When the charge transport material is added to the charge generation layer, as mentioned above, it is preferable that the amount of charge transport material be in the range of 20 to 200 wt % of the total weight of the binder resin for use in the charge generation layer.

In the single-layered photoconductive layer, it is preferable that the amount of the mixture of titanyltetraazaporphyrin compounds be in the range of 5 to 95 wt % of the entire weight of the binder resin for use in the photoconductive layer. In this case, the thickness of the single-layered photoconductive layer is preferably in the range of 10 to 100 μm. When a charge transport material is added to the single-layered photoconductive layer, it is preferable that the amount of the charge transport material be in the range of 30 to 200 wt % of the entire weight of the binder resin for use in the single-layered photoconductive layer.

There can be employed a photoconductive layer comprising a high-molecular weight charge transport material and the mixture of titanyltetraazaporphyrin compounds according to the present invention. In this case, it is preferable that the amount of the mixture of titanyltetraazaporphyrin compounds be in the range of 5 to 95 wt % of the entire weight of the high-molecular weight charge transport material. In this case, it is preferable that the thickness of the photoconductive layer be in the range of 10 to 100 μm.

To improve the chargeability, the photoconductive layer may further comprise a phenol compound, a hydroquinone compound, a hindered phenol compound, a hindered amine compound, and a compound having a hindered amine and a hindered phenol in a molecule thereof.

For the electroconductive support, there can be employed a metallic plate, drum or foil made of aluminum, nickel, copper, titanium, gold or stainless steel; a plastic film on which an electroconductive material such as aluminum, nickel, copper, titanium, gold, tin oxide or indium oxide is deposited; and a sheet of paper or a plastic film, which may be formed in a drum, coated with an electroconductive material.

The electrophotographic photoconductor of the present invention may further comprise an intermediate layer which is provided between the electroconductive support and the photoconductive layer, as previously mentioned. The intermediate layer comprises a resin as the main component. The photoconductive layer is provided on the intermediate layer by coating method using a solvent, so that it is desirable that the resin for use in the intermediate layer have high resistance against general-purpose organic solvents.

Preferable examples of the resin for use in the intermediate layer include water-soluble resins such as polyvinyl alcohol, casein and sodium polyacrylate; alcohol-soluble resins such as copolymer nylon and methoxymethylated nylon; and hardening resins with three-dimensional network such as polyurethane, melamine resin, phenolic resin, alkyd-melamine resin and epoxy resin.

The intermediate layer may further comprise finely-divided particles of metallic oxides such as titanium oxide, silica, alumina, zirconium oxide, tin oxide and indium oxide in order to prevent the occurrence of Moire and reduce the residual potential.

Similar to the previously mentioned photoconductive layer, the intermediate layer can be provided on the electroconductive support by coating method, using an appropriate solvent.

Further, the intermediate layer for use in the present invention may be prepared using a coupling agent such as a silane coupling agent, titanium coupling agent or chromium coupling agent. Furthermore, to prepare the intermediate layer, $Al_2O_3$ may be deposited on the electroconductive support by anodizing process, or an organic material such as poly-para-xylylene (parylene), or an inorganic material such as $SiO_2$, $SnO_2$, $TiO_2$, ITO or $CeO_2$ ray be deposited on the electroconductive support by vacuum thin-film forming method.

It is proper that the thickness of the intermediate layer be 5 μm or less.

The electrophotographic photoconductor according to the present invention may further comprise a protective layer which is provided on the photoconductive layer, as previously mentioned.

The protective layer for use in the present invention comprises a resin. Examples of such a resin for use in the protective layer include ABS resin, ACS resin, copolymer of olefin and vinyl monomer, chlorinated polyether, allyl resin, phenolic resin, polyacetal, polyamide, polyamideimide, polyacrylate, polyallyl sulfone, polybutylene, polybutylene terephthalate, polycarbonate, polyether sulfone, polyethylene, polyethylene terephthalate, polyimide, acrylic resin, polymethylpentene, polypropylene, polyphenylene oxide, polysulfone, polystyrene, AS resin, butadiene-styrene copolymer, polyurethane, polyvinyl chloride, polyvinylidene chloride and epoxy resin.

The protective layer may further comprise a fluorine-containing resin such as polytetrafluoroethylene, and a silicone resin to improve the abrasion resistance. In addition, inorganic materials such as titanium oxide, tin oxide and potassium titanate may be dispersed in the above-mentioned fluorine-containing resin and silicone resin.

The protective layer may be provided on the photoconductive layer by the conventional coating method.

The thickness of the protective layer is preferably in the range of about 0.1 to 10 μm. Furthermore, a vacuum-deposited thin film of a-C or a-SiC may be used as the protective layer in the present invention.

The charge transport material for use in the photoconductive layer include a positive hole transport material and an electron transport material.

There can be employed any conventional positive hole transport materials, for example, poly-N-carbazole and derivatives thereof, poly-γ-carbazolyl ethylglutamate and derivatives thereof, a condensation product of pyrene and formaldehyde and derivatives thereof, polyvinyl pyrene, polyvinyl phenanthrene, oxazole derivatives, imidazole derivatives, triphenylamine derivatives, and the following compounds (A) to (R).

Compound (A) described in Japanese Laid-Open Patent Applications Nos. 55-154955 and 55-156954:

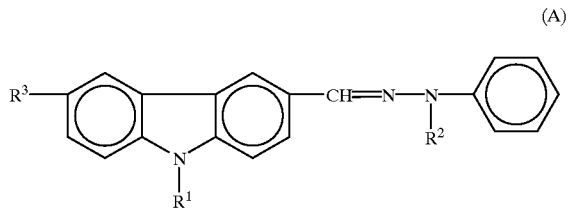

(A)

wherein $R^1$ is methyl group, ethyl group, 2-hydroxyethyl group, or 2-chloroethyl group; $R^2$ is methyl group, ethyl group, benzyl group, or phenyl group; and $R^3$ is a hydrogen atom, a chlorine atom, a bromine atom, an alkyl group having 1 to 4 carbon atoms, an alkoxyl group having 1 to 4 carbon atoms, a dialkylamino group, or nitro group.

Examples of the above compound of formula (A) are 9-ethylcarbazole-3-aldehyde-1-methyl-1-phenylhydrazone, 9-ethylcarbazole-3-aldehyde-1-benzyl-1-phenylhydrazone, and 9-ethylcarbazole-3-aldehyde-1,1-diphenylhydrazone.

Compound (B) described in Japanese Laid-Open Patent Application No. 55-52063:

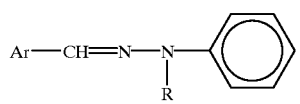

(B)

wherein Ar is a naphthalene ring, anthracene ring or styryl ring, each of which may have a substituent, a pyridine ring, furan ring, or thiophene ring; and R is an alkyl group or benzyl group.

Examples of the above compound of formula (B) are 4-diethylaminostyryl-3-aldehyde-1-methyl-1-phenylhydrazone, and 4-methoxynaphthalene-1-aldehyde-1-benzyl-1-phenylhydrazone.

Compound (C) described in Japanese Laid-Open Patent Application No. 56-81850:

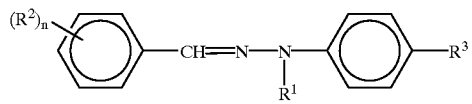

(C)

wherein $R^1$ is an alkyl group, benzyl group, phenyl group or naphthyl group; $R^2$ is a hydrogen atom, an alkyl group having 1 to 3 carbon atoms, an alkoxyl group having 1 to 3 carbon atoms, a dialkylamino group, a diaralkylamino group, or a diarylamino group; n is an integer of 1 to 4, and when n is 2 or more, $R^2$ may be the same or different; and $R^3$ is a hydrogen atom or methoxy group.

Examples of t he above compound of formula (C) are 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenyahydrazone, 4-methoxybenzaldehyde-1-benzyl-1-(4-methoxy)phenyl hydrazone, 4-diphenylaminobenzaldehyde-1-benzyl-1-phenylhydrazone, and 4-dibenzylaminobenzaldehyde-1,1-diphenylhydrazone.

Compound (d) described in Japanese Laid-Open Patent Application No. 51-10983:

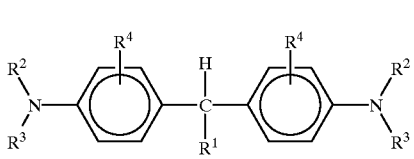

(D)

wherein $R^1$ is an alkyl group having 1 to 11 carbon atoms, a substituted or unsubstituted phenyl group, or a heterocyclic group; $R^2$ and $R^3$ are each independently a hydrogen atom, an alkyl group having 1 to 4 carbon atoms, a hydroxyalkyl group, chloroalkyl group, or a substituted or unsubstituted aralkyl group, and $R^2$ and $R^3$ may form a nitrogen-containing heterocyclic ring in combination; and $R^4$, which may be the same or different, each is a hydrogen atom, an alkyl group having 1 to 4 carbon atoms, an alkoxyl group, or a halogen atom.

Examples of the above compound of formula (D) are 1,1-bis(4-dibenzylaminophenyl)propane, tris(4-diethylaminophenyl)methane, 1,1-bis(4-dibenzylaminophenyl)propane, and 2,2'-dimethyl-4,4'-bis(diethylamino)triphenylmethane.

Compound (E) described in Japanese Laid-Open Patent Application No. 51-94829;

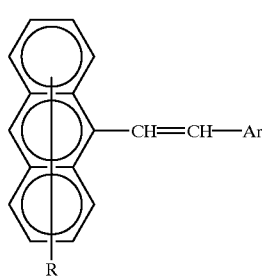

(E)

wherein R is a hydrogen atom or a halogen atom; and Ar is a substituted or unsubstituted phenyl group, naphthyl group, anthryl group, or carbazolyl group.

Examples of the above compound of formula (E) are 9-(4-diethylaminostyryl)anthracene, and 9-bromo-10-(4-diethylaminostyryl)anthracene.

Compound (F) described in Japanese Laid-Open Patent Application No. 52-128373:

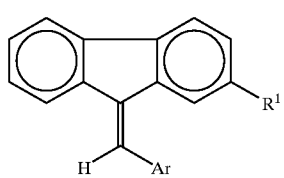

(F)

wherein $R^1$ is a hydrogen atom, a halogen atom, cyano group, an alkoxyl group having 1 to 4 carbon atoms, or an alkyl group having 1 to 4 carbon atoms; and Ar is

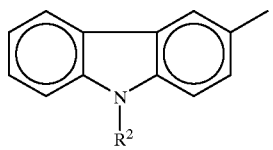

or

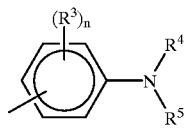

in which $R^2$ is an alkyl group having 1 to 4 carbon atoms; $R^3$ is a hydrogen atom, a halogen atom, an. alkyl group having 1 to 4 carbon atoms, an alkoxyl group having 1 to 4 carbon atoms, or a dialkylamino group; n is an integer of 1 or 2, and when n is 2, $R^3$ may be the same or different; and $R^4$ and $R^5$ are each a hydrogen atom, a substituted or unsubstituted alkyl group having 1 to 4 carbon atoms, or a substituted or unsubstituted benzyl group.

Examples of the above compound of formula (F) are 9-(4-dimethylaminobenzylidene)fluorene, and 3-(9-fluorenylidene)-9-ethylcarbazole.

Compound (G) described in Japanese Laid-Open Patent Application No. 56-29245:

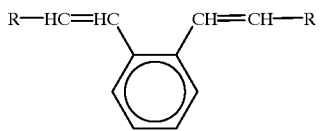

(G)

wherein R is carbazolyl group, pyridine group, thienyl group, indolyl group, furyl group, a substituted or unsubstituted phenyl group, a substituted or unsubstituted styryl group, a substituted or unsubstituted naphthyl group, or a substituted or unsubstituted anthryl group, each of which may have a substituent selected from the group consisting of a dialkylamino group, an alkyl group, an alkoxyl group, carboxyl group and an ester group thereof, a halogen atom, cyano group, an aralkylamino group, an N-alkyl-N-aralkylamino group, amino group, nitro group and acetylamino group.

Examples of the above compound of formula (G) are 1,2-bis(4-diethylaminostyryl)benzene, and 1,2-bis(2,4-dimethoxystyryl)benzene.

Compound (H) Described in Japanese Laid-Open Patent Application No. 58-58552:

(H)

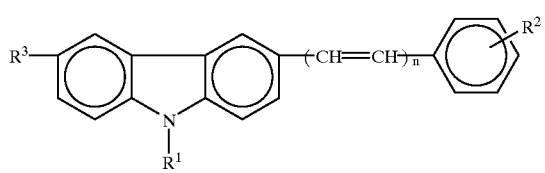

wherein $R^1$ is a lower alkyl group, a substituted or unsubstituted phenyl group, or benzyl group; $R^2$ and $R^3$ are each a hydrogen atom, a lower alkyl group, a lower alkoxyl group, a halogen atom, nitro group, or an amino group which may have as a substituent a lower alkyl group or benzyl group; and n is an integer of 1 or 2.

Examples of the above compound of formula (H) are 3-styryl-9-ethylcarbazole, and 3-(4-methoxystyryl)-9-ethylcarbazole.

Compound (I) described in Japanese Laid-Open Patent Application No. 57-73075:

(I)

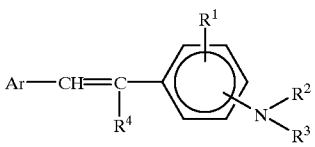

wherein $R^1$ is a hydrogen atom, an alkyl group, an alkoxyl group, or a halogen atom; $R^2$ and $R^3$ are each an alkyl group, a substituted or unsubstituted aralkyl group, or a substituted or unsubstituted aryl group; $R^4$ is a hydrogen atom, or a substituted or unsubstituted phenyl group; and Ar is a substituted or unsubstituted phenyl group, or a substituted or unsubstituted naphthyl group.

Examples of the above compound of formula (I) are 4-diphenylaminostilbene, 4-dibenzylaminostilbene, 4-ditolylaminostilbene, 1-(4-diphenylaminostyryl)naphthalene, and 1-(4-diethylaminostyryl)naphthalene.

Compound (J) described in Japanese Laid-Open Patent Application No. 58-198043:

(J)

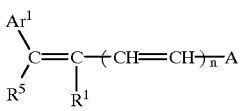

wherein n is an integer of 0 or 1; $R^1$ is a hydrogen atom, an alkyl group, or a substituted or unsubstituted phenyl group; $Ar^1$ is a substituted or unsubstituted aryl group; $R^5$ is a substituted or unsubstituted alkyl group, or a substituted or unsubstituted aryl group; and A is 9-anthryl group, a substituted or unsubstituted carbazolyl group, or

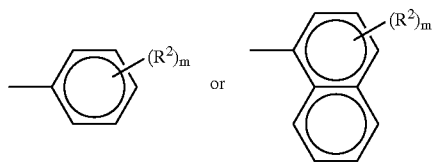

in which $R^2$ is a hydrogen atom, an alkyl group, an alkoxyl group, a halogen atom, or

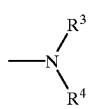

in which $R^3$ and $R^4$ are each an alkyl group, a substituted or unsubstituted aralkyl group, or a substituted or unsubstituted aryl group, and $R^3$ and $R^4$ may be the same or different, or form a ring in combination; m is an integer of 0 to 3, and when m is 2 or more, $R^2$ may be the same or different; and when n=0, A and $R^1$ may form a ring in combination.

Examples of the above compound of formula (J) are 4'-diphenylamino-α-phenylstilbene, and 4'-bis(methylphenyl)amino-α-phenylstilbene.

Compound (K) described in Japanese Laid-Open Patent Application No. 49-105537:

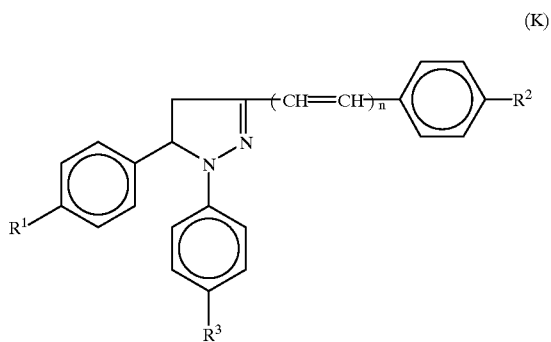

(K)

wherein $R^1$, $R^2$ and $R^3$ are each a hydrogen atom, a lower alkyl group, a lower alkoxyl group, a dialkylamino group, or a halogen atom; and n igs an integer of 0 or 1.

Examples of the above compound of formula (K) include 1-phenyl-3-(4-diethyaminostyryl)-5-(4-diethylaminophenyl)pyrazoline and 1-phenyl-3-(4-dimethylaminostyryl)-5-(4-dimethylaminophenyl)pyrazoline.

Compound (L) described in Japanese Laid-Open Patent Application No. 52-139066:

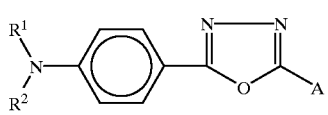

(L)

wherein $R^1$ and $R^2$ are each a substituted or unsubstituted alkyl group, or a substituted or unsubstituted aryl group; and A is a substituted amino group, a substituted or unsubstituted aryl group, or an allyl group.

Examples of the above compound of formula (L) are 2,5-bis(4-diethylaminophenyl)-1,3,4-oxadiazole, 2-N,N-diphenylamino-5-(4-diethylaminophenyl)-1,3,4-oxadiazole, and 2-(4-dimethylaminophenyl)-5-(4-diethylaminophenyl)-1,3,4-oxadiazole.

Compound (M) Described in Japanese Laid-Open Patent Application No. 52-139065:

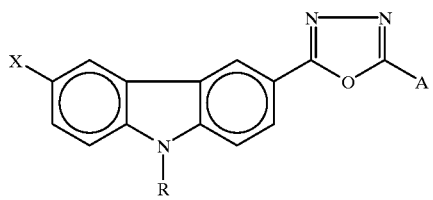

(M)

wherein X is a hydrogen atom, a lower alkyl group, or a halogen atom; R is a substituted or unsubstituted alkyl group, or a substituted or unsubstituted aryl group; and A is a substituted amino group, or a substituted or unsubstituted aryl group.

Examples of the above compound of formula (M) are 2-N,N-diphenylamino-5-(N-ethylcarbazol-3-yl)-1,3,4-oxadiazole, and 2-(4-diethylaminophenyl)-5-(N-ethylcarbazol-3-yl)-1,3,4-oxadiazole.

Compound (N) Described in Japanese Laid-Open Patent Application No. 58-32372:

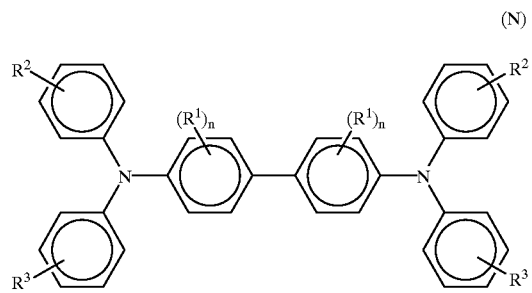

(N)

wherein $R^1$ is a lower alkyl group, a lower alkoxyl group, or a halogen atom; n is an integer of 0 to 4; and $R^2$ and $R^3$ may be the same or different, and are each a hydrogen atom, a lower alkyl group, a lower alkoxyl group, or a halogen atom.

Examples of the benzidine compound represented by formula (N) are N,N'-diphenyl-N,N'-bis(3-methylphenyl)-[1,1'-biphenyl]-4,4'-diamine, and 3,3'-dimethyl-N,N,N',N'-tetrakis(4-methylphenyl)-[1,1'-biphenyl]-4,4'-diamine.

Compound (O) described in Japanese Laid-Open Patent Application No. 2-178669:

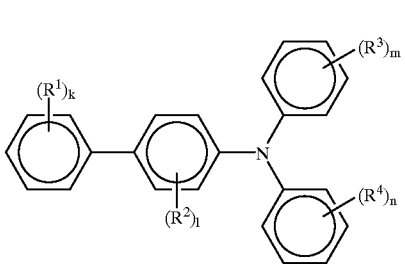

(O)

wherein $R^1$, $R^3$ and $R^4$ are each a hydrogen atom, amino group, an alkoxyl group, a thioalkoxyl group, an aryloxy group, methylenedioxy group, a substituted or unsubstituted alkyl group, a halogen atom, or a substituted or unsubstituted aryl group; $R^2$ is a hydrogen atom, an alkoxyl group, a substituted or unsubstituted alkyl group, or a halogen atom, provided that $R^1$, $R^2$, $R^3$ and $R^4$ are not hydrogen atoms at the same time; and k, l, m and n are each an integer of 1 to 4, and when each is an integer of 2, 3 or 4, $R^1$, $R^2$, $R^3$ and $R^4$ may be independently the same or different.

Examples of the biphenylamine compound represented by formula (O) are 4'-methoxy-N,N-diphenyl-[1,1'-biphenyl]-4-amine, 4'-methyl-N,N'-bis(4-methylphenyl)-[1,1'-biphenyl]-4-amine, and 4'-methoxy-N,N'-bis(4-methylphenyl)-[1,1'-biphenyl]-4-amine.

Compound (P) described in Japanese Laid-Open Patent Application No. 3-285960:

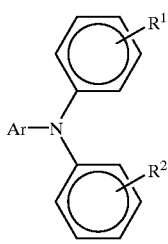 (P)

wherein Ar is a condensed polycyclic hydrocarbon group having 18 or less carbon atoms; and $R^1$ and $R^2$ are each a hydrogen atom, a halogen atom, a substituted or unsubstituted alkyl group, an alkoxyl group, or a substituted or unsubstituted phenyl group, and $R^1$ and $R^2$ may be the same or different.

Examples of the triarylamine compound represented by formula (P) are 1-diphenylaminopyrene, and 1-di(p-tolylamino)pyrene.

Compound (Q) described in Japanese Laid-Open Patent Application No. 62-98394:

 (Q)

wherein Ar is a substituted or unsubstituted aromatic hydrocarbon group; and A is

in which Ar' is a substituted or unsubstituted aromatic hydrocarbon group; and $R^1$ and $R^2$ are each a substituted or unsubstituted alkyl group, or a substituted or unsubstituted aryl group.

Examples of the diolefin aromatic compound represented by formula (Q) are 1,4-bis(4-diphenylaminostyryl)benzene, and 1,4-bis[4-di(p-tolyl)aminostyryl]benzene.

Compound (R) described in Japanese Laid-Open Patent Application No. 4-230764:

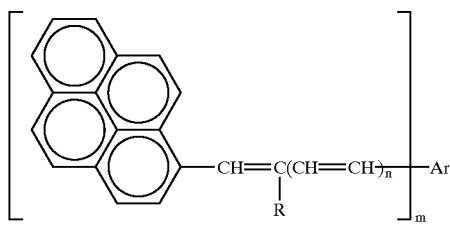 (R)

wherein Ar is an aromatic hydrocarbon group; R is a hydrogen atom, a substituted or unsubstituted alkyl group, or a substituted or unsubstituted aryl group; and n is an integer of 0 or 1, and m is an integer of 1 or 2, and when n=0 and m=1, Ar and R may form a ring in combination.

Examples of the styrylpyrene compound represented by formula (R) are 1-(4-diphenylamininostyryl)pyrene, and 1-[4-di(p-tolyl)aminostyryl]pyrene.

Examples of the electron transport material for use in the present invention are chloroanil, bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophen-4-one, and 1,3,7-trinitrodibenzothiophene-5,5-dioxide.

In particular, the following electron transport materials of formulas (S) (T) and (U) are preferably employed because of their excellent electron transporting performance.

The above-mentioned charge transport materials may be used alone or in combination.

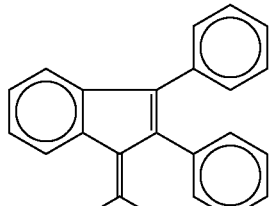 (S)

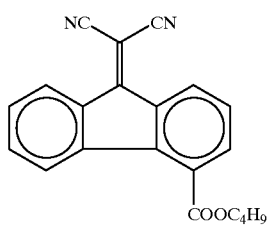 (T)

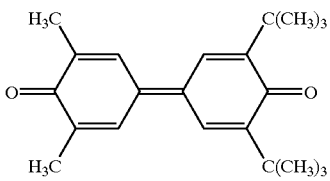 (U)

The mixture of titanyltetraazaporphyrin compounds of formula (1) according to the present invention is useful as the photoconductive material for use in the electrophotographic photoconductor, and in addition, as the electronic device in the solar battery and the optical disk in the field of electronics.

Other features of this invention will become apparent in the course of the following description of exemplary embodiments, which are given for illustration of the invention and are not intended to be limiting thereof.

EXAMPLE 1—1

[Preparation of Mixture No. 1]

19.48 g (152.0 mmol) of phthalonitrile, 1.03 g (8.00 mmol) of 2,3-dicyanopyridine, 14.97 g (44.00 mmol) of tetra-n-butyl o-titanate, 4.80 g (80.00 mmol) of urea, and 24.48 g of 1-octanol were mixed and heated with stirring at 150 to 161° C. in a stream of nitrogen for 6 hours. Thereafter, the above mixture was cooled to room temperature, and further stirred under reflux for 30 minutes, with 80 ml of methanol being added thereto.

After cooled to room temperature, the resultant crystals separated by filtration were successively washed with toluene, methanol and water, and dried with the application of heat under reduced pressure, whereby 19.38 g of a mixture of titanyltetraazaporphyrin compounds (mixture No. 1) in the form of a blue powder was obtained in an 84.0% yield.

The results of the elemental analysis of the thus obtained mixture No. 1 were as follows:

|       | % C   | % H  | % N   |
|-------|-------|------|-------|
| Found | 66.74 | 2.64 | 19.45 |

To confirm the reproducibility of the preparation method of the mixture of titanyltetraazaporphyrin compounds, the procedure for preparation of the mixture No. 1 was repeated 10 times in the same manner as mentioned above. According to the results of elemental analysis of the obtained mixtures, the scattering of the found values (%) of C, H and N was within 3%, It was thus confirmed that the mixture of titanyltetraazaporphyrin compounds of the present invention was produced by the method of the present invention with high reproducibility.

The X-ray diffraction spectrum of the mixture of titanyltetraazaporphyrin compounds (mixture No. 1) in the form of a powder was measured under the following conditions:

| X-ray tube:     | Cu (wavelength: 1.54 Å) |
|-----------------|--------------------------|
| Voltage:        | 50 kV                    |
| Current:        | 30 mA                    |
| Scanning speed: | 2 deg/min.               |
| Scanning scope: | 3 to 40 deg.             |
| Time constant:  | 2 sec                    |

FIG. 1 is an X-ray diffraction spectrum of the mixture No. 1 obtained in Example 1—1. As shown in FIG. 1, the strongest peak appears at a Bragg angle ($2\theta$) of 26.2°.

The mass spectrometric analysis of the mixture of titanyltetraazaporphyrin compounds (mixture No. 1) was carried out under the following conditions:
(LC/MC Apparatus)
  Manufacturer: JEOL
  Model: Mass Analyzer "MS700"
(Measuring Conditions)
  Ionization: Electrospray ionization (ESI) +ion mode
  Flow rate: 25 $\mu$L/min
  Injection mode: Infusion
  Ring voltage: 80 V
  Skimmer voltage: 0 V For preparation of a sample to be subjected to the mass spectrometric analysis, the mixture No. 1 was dissolved in formic acid to prepare a solution, and the thus prepared solution was diluted with a 50% aqueous solution of formic acid so that the concentration of the mixture No. 1 was adjusted to 50 ppm.

Figure 10:
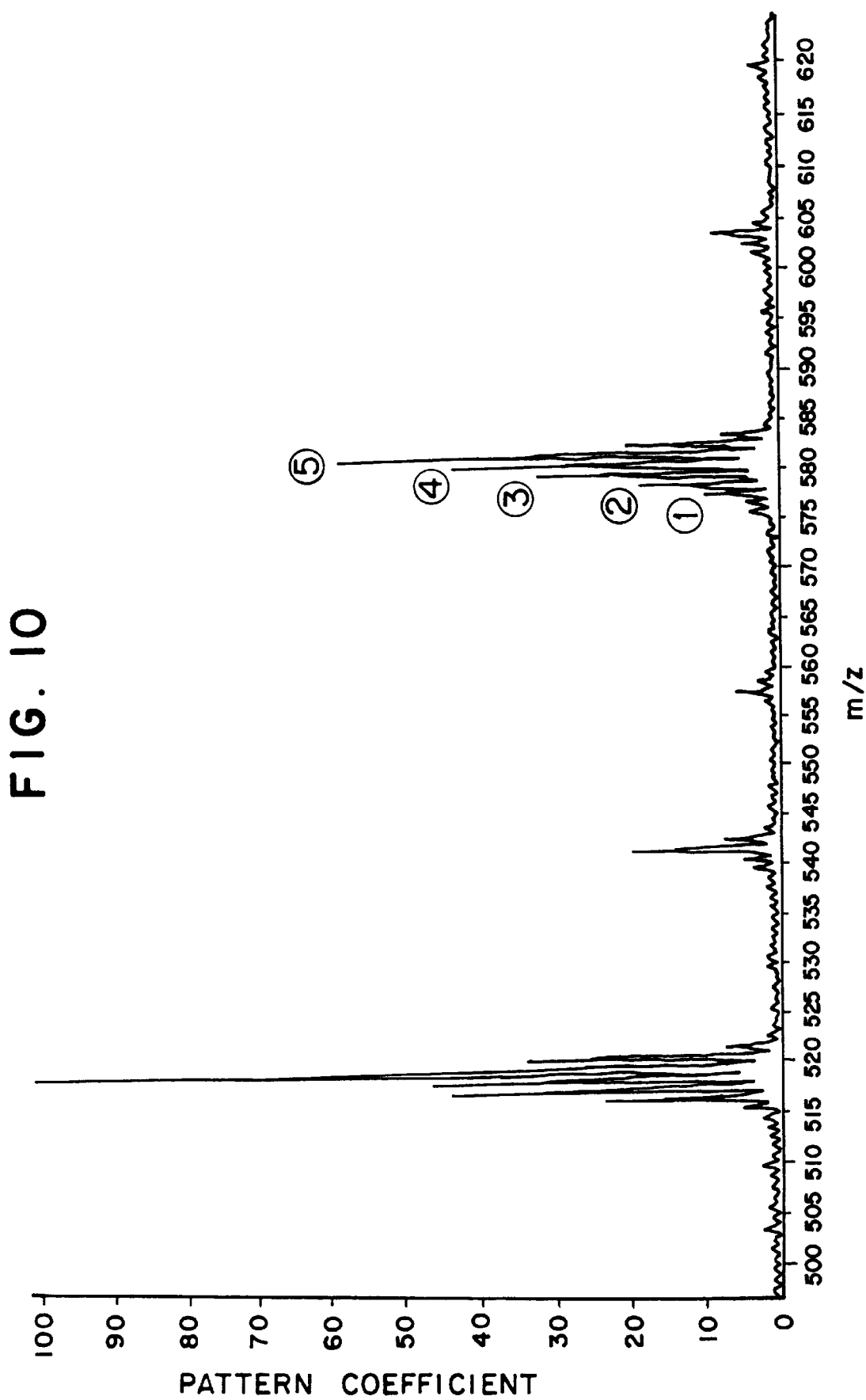
FIG. 10 is a chart showing the results of mass spectrometric analysis of a mixture (No. 1) of titanyltetraazaporphyrin compounds obtained in Example 1—1.

The result of the mass spectrometric analysis of the mixture of titanyltetraazaporphyrin compounds (mixture No. 1) is shown in FIG. 10. The fragment peaks ① to ⑤ in FIG. 10 correspond to the molecular weights of compounds as shown below:

| ① | $C_{32}H_{16}N_8OTi$:    | 576.42 m/z |
| ② | $C_{31}H_{15}N_9OTi$:    | 577.41 m/z |
| ③ | $C_{30}H_{14}N_{10}OTi$: | 578.39 m/z |
| ④ | $C_{29}H_{13}N_{11}OTi$: | 579.38 m/z |
| ⑤ | $C_{28}H_{12}N_{12}OTi$: | 580.37 m/z |

Namely, it is confirmed that there are the following five titanyltetraazaporphyrin compounds ① to ⑤ in the mixture:

A titanyltetraazaporphyrin compound ① of formula (1) in which A, B, C and D are each an unsubstituted benzene ring. The molecular weight is about 576 m/z.

A titanyltetraazaporphyrin compound ② of formula (1) in which three of A, B, C and D are each an unsubstituted benzene ring, and the rest thereof is an unsubstituted pyridine ring. The molecular weight is about 577 m/z.

A titanyltetraazaporphyrin compound ③ of formula (1) in which two of A, B, C and D are each an unsubstituted benzene ring, and the rest thereof are each an unsubstituted pyridine ring. The molecular weight is about 578 m/z.

A titanyltetraazaporphyrin compound ④ of formula (1) in which one of A, B, C or D is an unsubstituted benzene ring, and the rest thereof are each an unsubstituted pyridine ring. The molecular weight is about 579 m/z.

A titanyltetraazaporphyrin compound ⑤ of formula (1) in which A, B, C and D are each an unsubstituted pyridine ring. The molecular weight is about 580 m/z.

EXAMPLES 1-2 to 1-7
[Preparation of Mixtures Nos. 2 to 7]

The procedure for preparation of the mixture No. 1 in Example 1—1 was repeated except that the mixing ratio of phthalonitrile to 2,3-dicyanopyridine in Example 1—1 was changed as shown in TABLE 1. Thus, mixtures of titanyltetraazaporphyrin compounds (mixtures Nos. 2 to 7) according to the present invention were obtained.

TABLE 1 also shows the yield, and TABLE 2 shows the results of elemental analysis and the strongest diffraction peak in terms of the Bragg angle ($2\theta$) in the X-ray diffraction spectrum of each mixture.

TABLE 1

|     | Mixture No. | Molar Ratio of Phthalonitrile to 2,3-dicyanopyridine | Yield (%) |
|-----|-------------|------------------------------------------------------|-----------|
| 1-1 | 1           | 19:1                                                 | 84.0      |
| 1-2 | 2           | 399:1                                                | 84.0      |
| 1-3 | 3           | 39:1                                                 | 84.3      |
| 1-4 | 4           | 15:1                                                 | 85.0      |
| 1-5 | 5           | 11:1                                                 | 83.3      |
| 1-6 | 6           | 7:1                                                  | 83.7      |
| 1-7 | 7           | 1:1                                                  | 69.2      |

TABLE 2

| Example No. | Mixture No. | Elemental Analysis (Found Value) | | | Peak in X-ray Diffraction Spectrum (°) |
|-------------|-------------|---|---|---|---|
|             |             | % C | % H | % N | |
| 1-1 | 1 | 66.74 | 2.64 | 19.45 | 26.2 |
| 1-2 | 2 | 66.80 | 2.69 | 19.06 | 27.2 |
| 1-3 | 3 | 66.53 | 2.70 | 19.13 | 26.1 |
| 1-4 | 4 | 66.74 | 2.64 | 19.55 | 26.2 |
| 1-5 | 5 | 66.47 | 2.77 | 19.63 | 26.1 |
| 1-6 | 6 | 66.40 | 2.69 | 20.06 | 26.2 |
| 1-7 | 7 | 66.22 | 2.68 | 20.67 | 6.9  |

EXAMPLE 1-8
[Preparation of Mixture No. 8]

80 g of concentrated sulfuric acid was cooled on an ice-water bath with stirring. 5.00 g of the mixture of titanyltetraazaporphyrin compounds (mixture No. 1) obtained in Example 1—1 was dissolved in small portions in the above-mentioned sulfuric acid over a period of 30 minutes. The thus obtained solution was stirred for about one hour, and thereafter, added dropwise to 500 g of ice-cold water.

After stirring for 30 minutes, the resultant crystals were separated by filtration, and repeatedly washed with water three times. After filtration, 28.9 g of a wet cake with a solid content of 17.3 wt % was obtained. The wet cake was dried by the application of heat thereto under reduced pressure, so that a mixture of titanyltetraazaporphyrin compounds was obtained.

Figure 2:
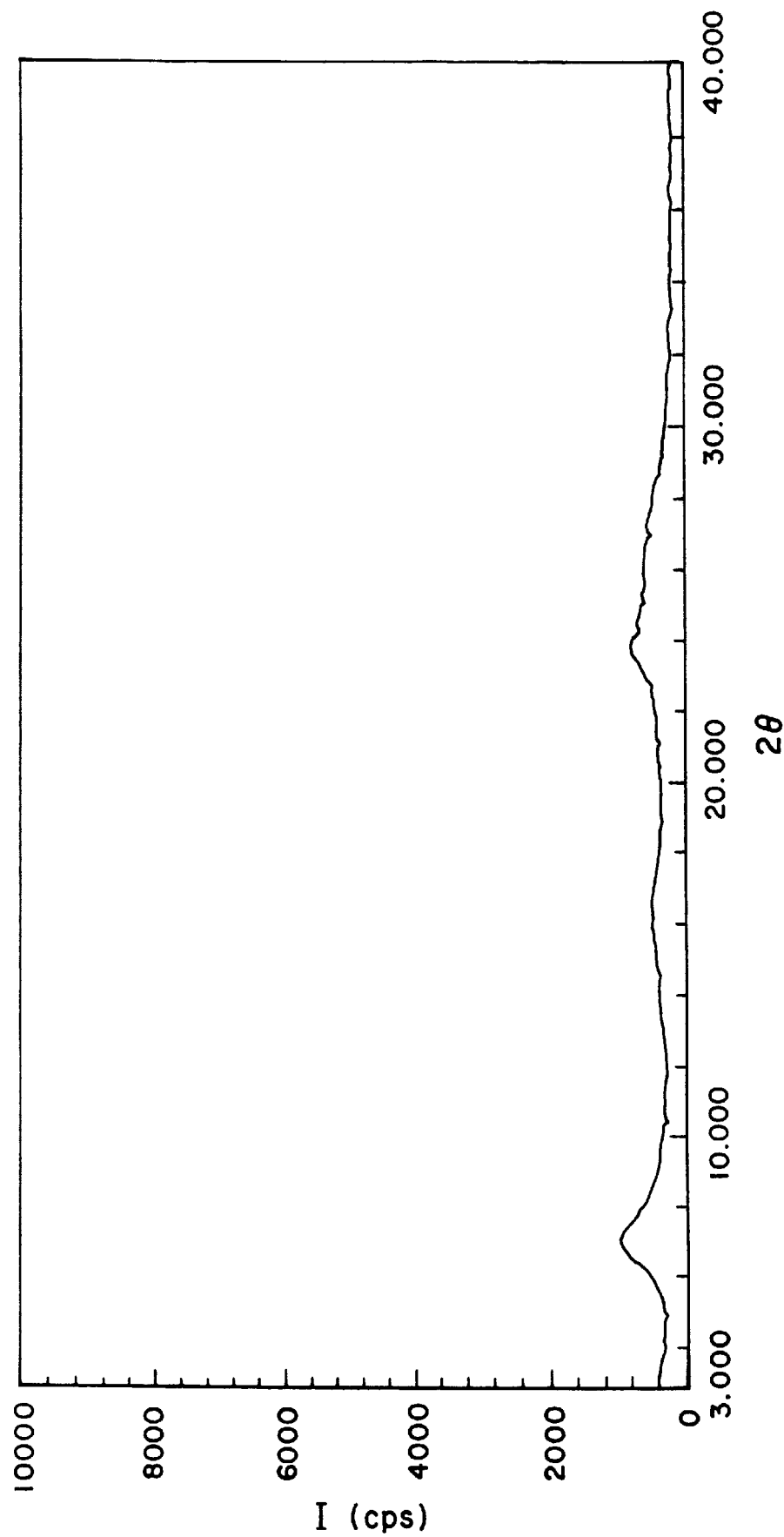
FIG. 2 is an X-ray diffraction spectrum of a mixture of titanyltetraazaporphyrin compounds in the form of a powder obtained by subjecting the mixture No. 1 to acid treatment in Example 1-8.

The X-ray diffraction spectrum of the thus obtained mixture of titanyltetraazaporphyrin compounds is shown in FIG. 2.

9.7 g of deionized water and 120 g of tetrahydrofuran were added to 17.3 g of the above obtained wet cake. The mixture was stirred at room temperature for 6 hours. After completion of stirring, the mixture was filtered off, and dried under reduced pressure, so that 2.72 g of a mixture of titanyltetraazaporphyrin compounds (mixture No. 8) was obtained in the form of blue crystals.

Figure 3:
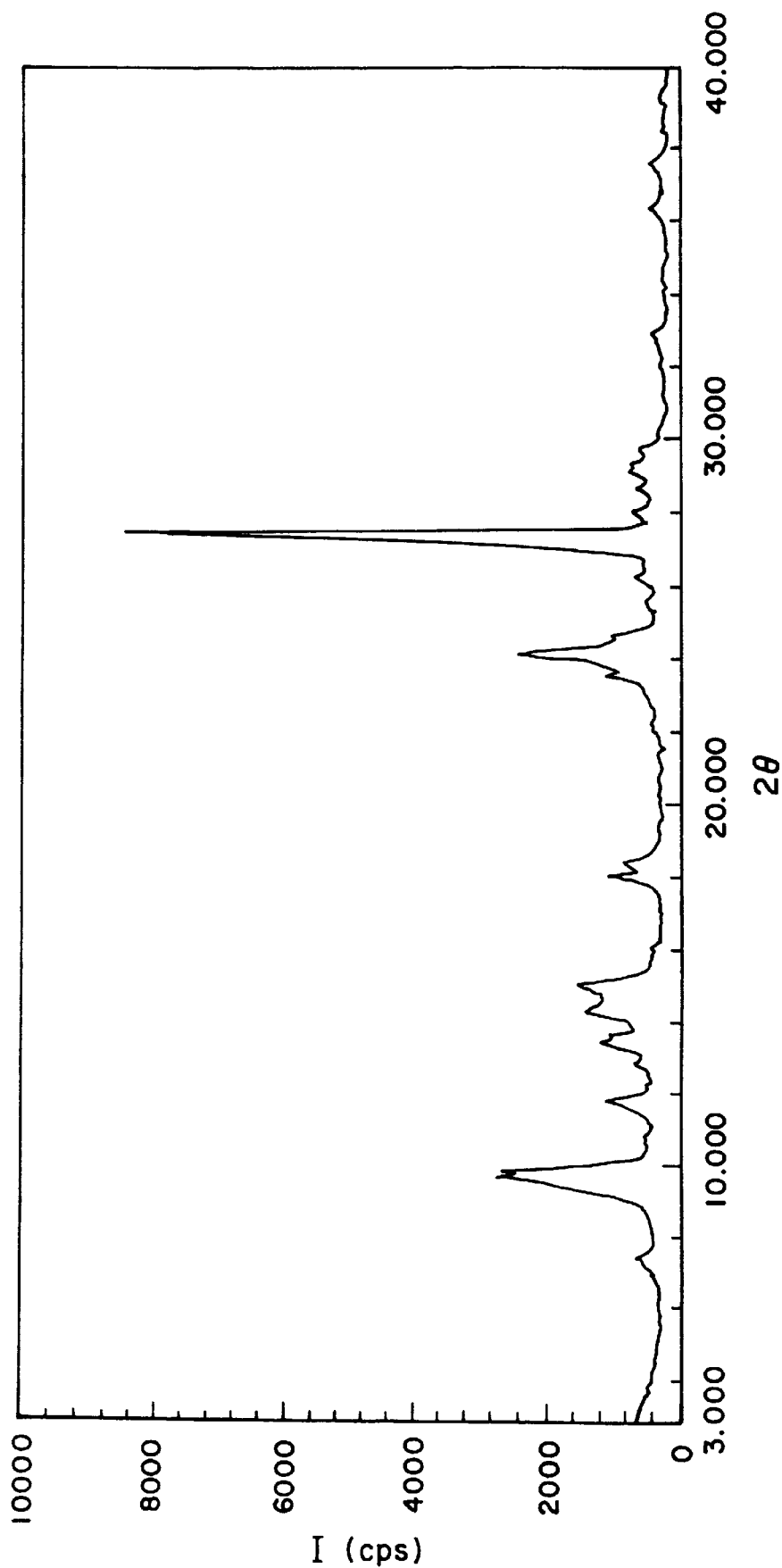
FIG. 3 is an X-ray diffraction spectrum of a mixture (No. 8) of titanyltetraazaporphyrin compounds in the form of a powder obtained in Example 1-8.

FIG. 3 is an X-ray diffraction spectrum of the mixture No. 8. The strongest diffraction peak appears at 27.2° in terms of the Bragg angle (2θ) in the X-ray diffraction spectrum.

TABLE 3 shows the results of elemental analysis and the strongest diffraction peak in terms of the Bragg angle (2θ) in the X-ray diffraction spectrum of the mixture No. 8.

EXAMPLES 1-9 TO 1-14
[Preparation of Mixtures Nos. 9 to 14]

The procedure for preparation of the mixture of titanyltetraazaporphyrin compounds (mixture No. 8) in Example 1-8 was repeated except that the mixture No. 1 initially employed in Example 1-8 was replaced by the mixtures Nos. 2 to 7, respectively in Examples 1-9 to 1-14.

Thus, mixtures of titanyltetraazaporphyrin compounds (mixtures Nos. 9 to 14) according to the present invention were obtained.

TABLE 3 shows the mixture number initially employed, the results of elemental analysis, and the strongest diffraction peak in terms of the Bragg angle (2θ) in the X-ray diffraction spectrum of each mixture.

TABLE 3

| Example No. | Mixture No. | Initially Employed Mixture | Elemental Analysis (Found Value) | | | Peak in X-ray Diffraction Spectrum (°) |
|---|---|---|---|---|---|---|
| | | | % C | % H | % N | |
| 1-8 | 8 | 1 | 65.71 | 2.57 | 19.58 | 27.2 |
| 1-9 | 9 | 2 | 66.46 | 2.61 | 19.19 | 27.2 |
| 1-10 | 10 | 3 | 65.79 | 2.54 | 19.45 | 27.3 |
| 1-11 | 11 | 4 | 65.81 | 2.59 | 19.58 | 27.3 |
| 1-12 | 12 | 5 | 65.42 | 2.59 | 19.70 | 27.3 |
| 1-13 | 13 | 6 | 65.05 | 2.50 | 19.98 | 27.2 |
| 1-14 | 14 | 7 | 64.98 | 2.50 | 20.10 | 6.9 |

EXAMPLE 1-15
[Preparation of Mixture No. 15]

The wet cake obtained in Example 1-8 was dried with the application of heat thereto under reduced pressure.

With the addition of 50 ml of tetrahydrofuran to 1.00 g of crystals thus obtained, the mixture was stirred under reflux for 6 hours. The mixture was cooled to room temperature, and filtered off.

The resultant residue was dried with the application of heat thereto under reduced pressure, whereby 0.97 g of a mixture of titanyltetraazaporphyrin compounds (mixture No. 15) was obtained in the form of a blue powder.

Figure 4:
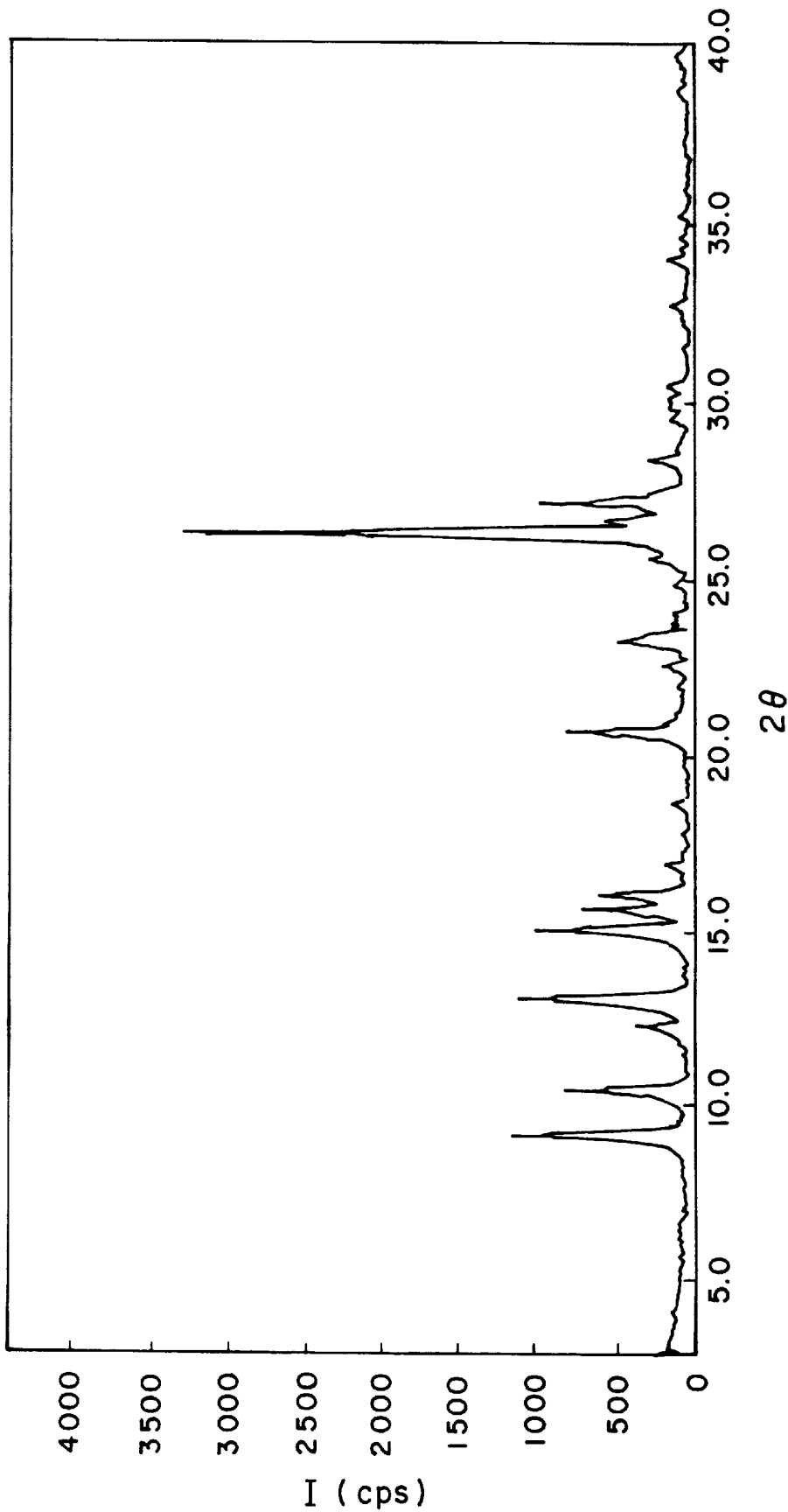
FIG. 4 is an X-ray diffraction spectrum of a mixture (No. 15) of titanyltetraazaporphyrin compounds in the form of a powder obtained in Example 1-15.

FIG. 4 is an X-ray diffraction spectrum of the mixture No. 15.

The results of elemental analysis, and the strongest diffraction peak in terms of the Bragg angle (2θ) in the X-ray diffraction spectrum of the mixture No. 15 are shown in TABLE 4.

EXAMPLES 1-16 TO 1-18
[Preparation of Mixtures Nos. 16 to 18]

The procedure for preparation of the mixture of titanyltetraazaporphyrin compounds (mixture No. 15) in Example 1-15 was repeated except that the mixture No. 1 initially employed in Example 1-15 was replaced by the mixtures Nos. 2, 3 and 6, respectively in Examples 1-16, 1-17 and 1-18.

Thus, mixtures of titanyltetraazaporphyrin compounds (mixtures Nos. 16 to 18) according to the present invention were obtained.

TABLE 4 shows the mixture number initially employed, the results of elemental analysis, and the strongest diffraction peak in terms of the Bragg angle (2θ) in the X-ray diffraction spectrum of each mixture.

Figure 5:
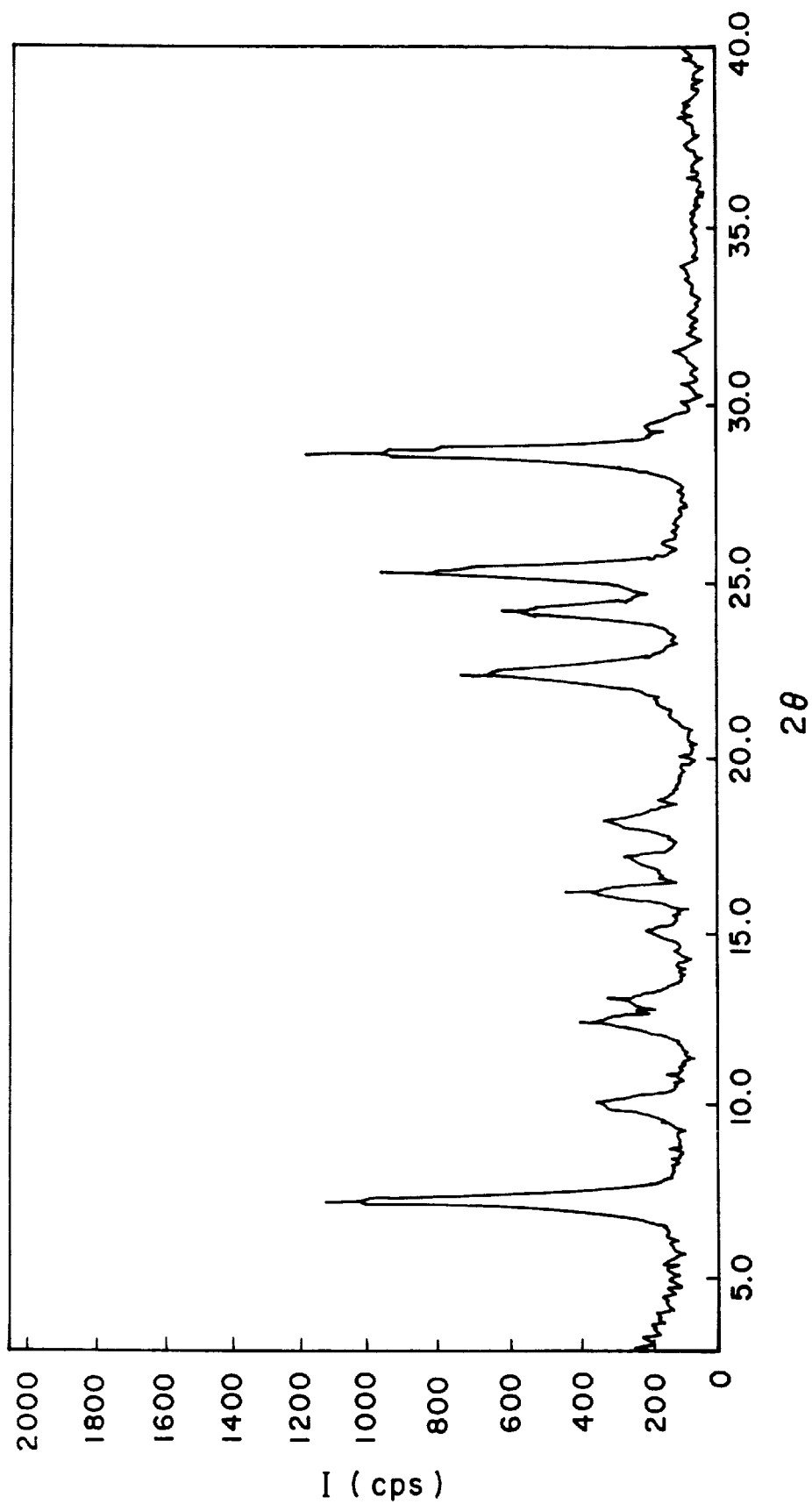
FIG. 5 is an X-ray diffraction spectrum of a mixture (No. 16) of titanyltetraazaporphyrin compounds in the form of a powder obtained in Example 1-16.

FIG. 5 is an X-ray diffraction spectrum of the mixture No. 16 prepared in Example 1-16.

TABLE 4

| Example No. | Mixture No. | Initially Employed Mixture | Elemental Analysis (Found Value) | | | Peak in X-ray Diffraction Spectrum (°) |
|---|---|---|---|---|---|---|
| | | | % C | % H | % N | |
| 1-15 | 15 | 1 | 65.73 | 2.59 | 19.61 | 26.2 |
| 1-16 | 16 | 2 | 66.29 | 2.60 | 19.23 | 28.5 |
| 1-17 | 17 | 3 | 65.81 | 2.58 | 19.39 | 26.1 |
| 1-18 | 18 | 6 | 65.85 | 2.66 | 20.02 | 26.2 |

EXAMPLE 1-19
[Preparation of Mixture No. 19]

30 g of concentrated sulfuric acid was cooled on an ice-water bath with stirring. 0.191 g (0.33 mmol) of the mixture of titanyltetraazaporphyrin compounds (mixture No. 7) obtained in Example 1-7 was mixed with 1.71 g (0.33×9 mmol) of titanyl phthalocyanine. The thus obtained mixture was dissolved in small portions in the abovementioned sulfuric acid over a period of 30 minutes. The thus obtained solution was stirred for 1.5 hours, and thereafter, added dropwise to 190 g of ice-cold water.

After stirring for 30 minutes, the reaction mixture was separated by filtration, and washed with water, whereby 12.7 g of a wet cake was obtained.

Thereafter, 3.3 g of deionized water and 40 g of tetrahydrofuran were added to 6.7 g of the above obtained wet cake. The mixture was stirred at room temperature for 6 hours. After completion of stirring, the reaction product was separated by filtration, and dried under reduced pressure, so that 0.94 g of a mixture of titanyltetraazaporphyrin compounds (mixture No. 19) was obtained in the form of blue crystals.

Figure 6:
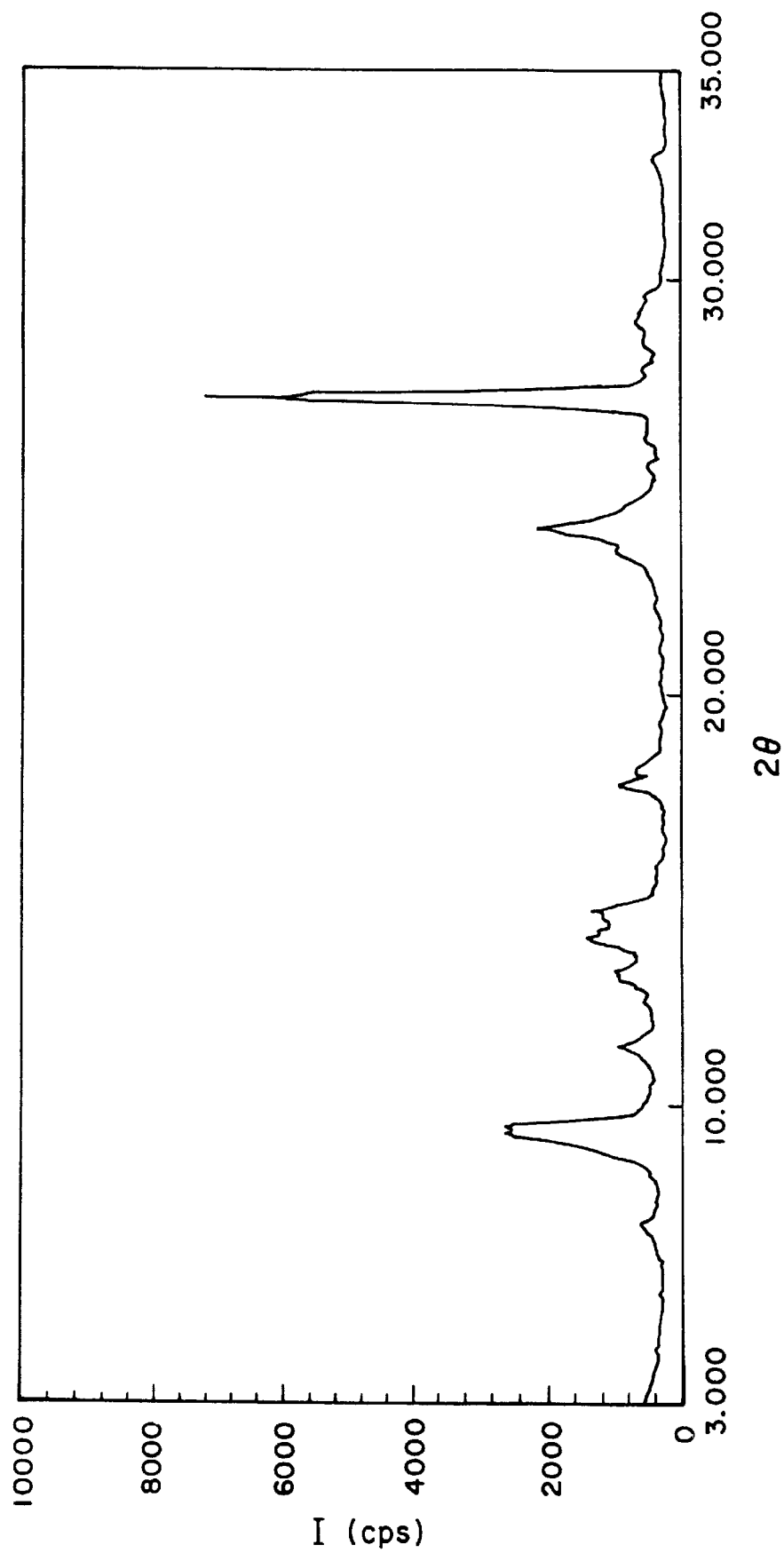
FIG. 6 is an X-ray diffraction spectrum of a mixture (No. 19) of titanyltetraazaporphyrin compounds in the form of a powder obtained in Example 1-19.

FIG. 6 is an X-ray diffraction spectrum of the mixture No. 19. The strongest diffraction peak appears at 27.2° in terms of the Bragg angle (2θ) in the X-ray diffraction spectrum.

COMPARATIVE EXAMPLE 1—1
[Preparation of Comparative Compound No. 1]

The procedure for preparation of the mixture No. 1 (mixture of titanyltetraazaporphyrin compounds) in Example 1-1 was repeated except that 152.0 mmol of phthalonitrile used in Example 1—1 was replaced by 152.0 mmol of 2,3-dicyanopyridine. Thus, a titanyltetrapyridotetraazaporphyrin (comparative compound No. 1) represented by the following formula (W) was obtained.

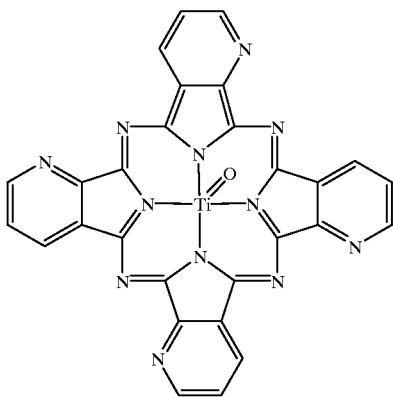
(W)

The mass spectrometric analysis of the comparative compound No. 1 was carried out under the same conditions as in Example 1—1.

Figure 11:
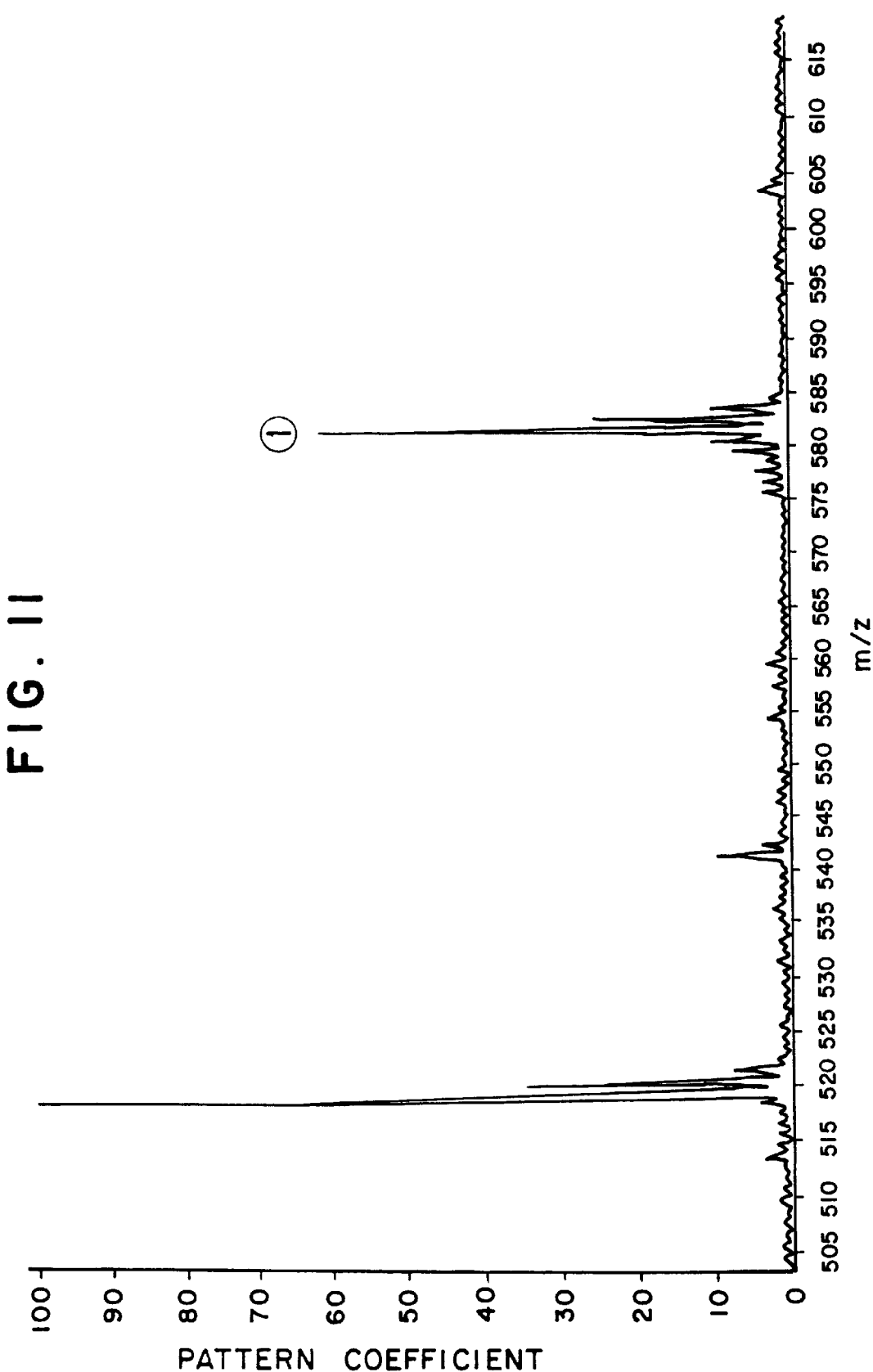
FIG. 11 is a chart showing the results of mass spectrometric analysis of a titanyltetrapyridoazaporphyrin compound (comparative compound No. 1) obtained in Comparative Example 1—1.

The result of the mass spectrometric analysis of the comparative compound No. 1 is shown in FIG. 11. The fragment peak ① in FIG. 11 corresponds to the molecular weight of the following compound:

$C_{28}H_{12}N_{12}OTi$: 580.37 m/z　②

It is thus confirmed that the comparative compound No. 1 is made of a single substance.

COMPARATIVE EXAMPLE 1-2
[Preparation of Comparative Compound No. 2]

55 g of concentrated sulfuric acid was cooled on an ice-water bath with stirring. 0.174 g (0.3 mmol) of the titanyltetrapyridotetraazaporphyrin (comparative compound No. 1) obtained in Comparative Example 1—1 was mixed with 3.29 g (0.3×19 mmol) of titanyl phthalocyanine. The thus obtained mixture was dissolved in small portions in the above-mentioned sulfuric acid over a period of 30 minutes. The thus obtained solution was stirred for 1.5 hours, and thereafter, added dropwise to 350 g of ice-cold water.

After stirring for 30 minutes, the reaction mixture was separated by filtration, and washed with water, whereby 24.0 g of a wet cake was obtained.

Thereafter, 3.07 g of deionized water and 40 g of tetrahydrofuran were added to 6.93 g of the above obtained wet cake. The mixture was stirred at room temperature for 6 hours. After completion of stirring, the reaction product was separated by filtration, and dried under reduced pressure, so that 0.96 g of a mixture of titanyltetrapyridotetraazaporphyrin and titanyl phthalocyanine (comparative compound No. 2) was obtained in the form of blue crystals.

COMPARATIVE EXAMPLE 1-3
[Preparation of comparative compound No. 3]

In accordance with the method described in Example 16 of Japanese Patent Publication 3-27111, a mixture of a plurality of copper tetraazaporphyrin compounds was prepared.

To be more specific, a mixture of 0.84 g (5.0 mmol) of pyridine-3,4-dicarboxylic acid, 14.07 g (95.0 mmol) of phthalic anhydride, 24.02 g (400 mmol) of urea, 2.48 g (25 mmol) of cuprous chloride, 0.04 g of ammonium molybdate·4hydrate, and 80 g of trichlorobenzene was stirred at 181-182° C. in a stream of nitrogen for 15 hours.

After the reaction mixture was allowed to stand at room temperature, the reaction mixture was stirred under reflux for 30 minutes with the addition of 80 ml of methanol, and thereafter cooled to room temperature.

The resultant crystals separated by filtration were. successively washed with toluene, methanol, a 3% aqueous solution of sodium hydroxide, water, 1% hydrochloric acid, and water, and dried at 100° C. under reduced pressure for 2 days, thereby obtaining a blue powder. The blue powder thus obtained was washed with dioxane in a Soxhlet apparatus for 2 days, and thereafter, dried at 100° C. under reduced pressure for 2 days. Thus, 12.51 g of a mixture of a plurality of copper tetraazaporphyrin compounds (comparative compound No. 3) was obtained in the form of a blue powder.

Figure 9:
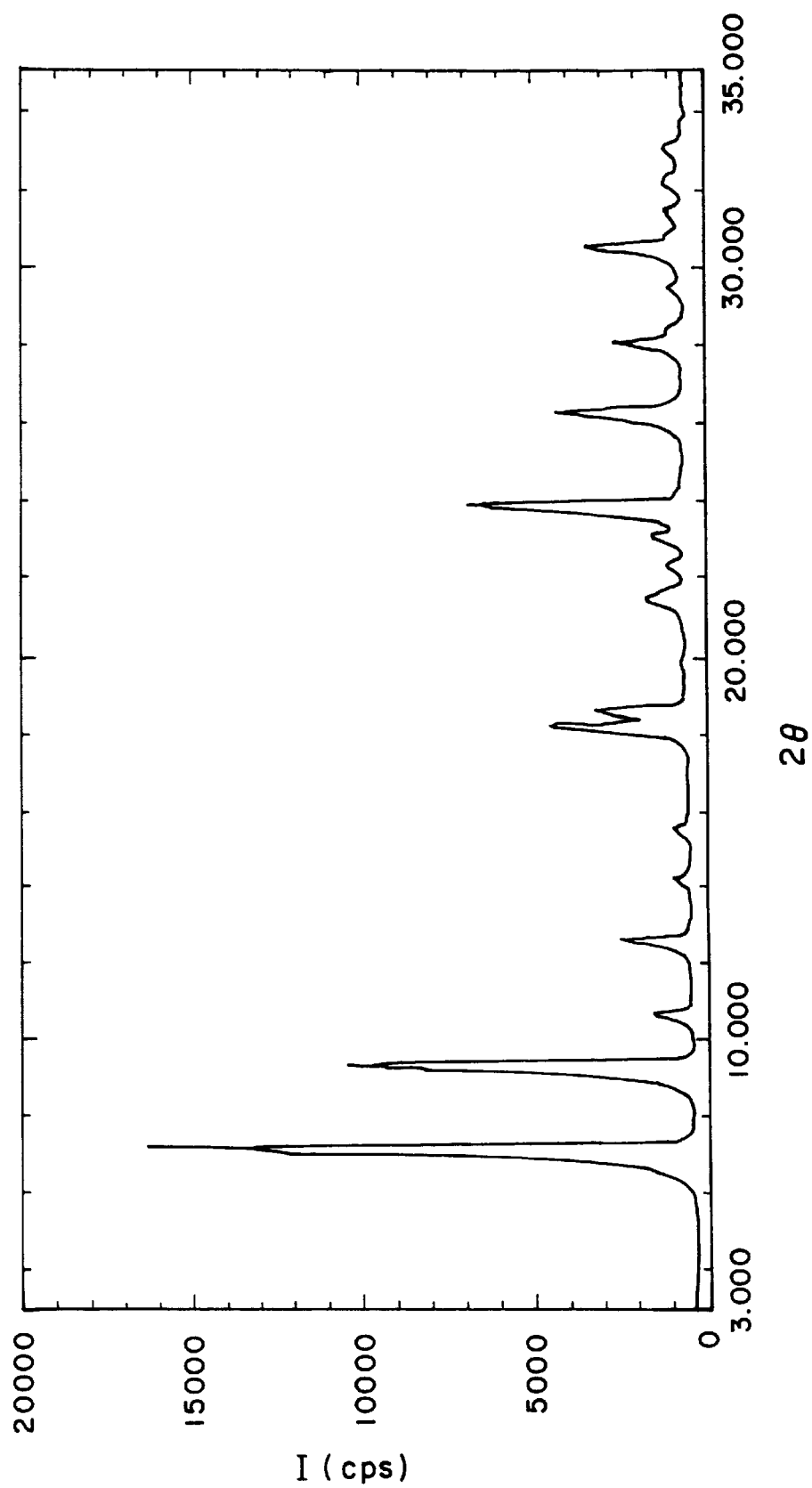
FIG. 9 is an X-ray diffraction spectrum of a mixture of copper-tetraazaporphyrin compounds in the form of a powder obtained in Comparative Example 1-3.

FIG. 9 is an X-ray diffraction spectrum of the comparative compound No. 3.

EXAMPLE 2-1
[Fabrication of Layered Photoconductor]
(Formation of intermediate layer)

A mixture of the following components was put into a ball mill and subjected to ball milling for 48 hours using alumina balls with a diameter of 10 mm so that a coating liquid for intermediate layer was prepared.

|  | Parts by Weight |
|---|---|
| Oil-free alkyd resin (Trademark "Beckolite M6401" made by Dainippon Ink & Chemicals, Incorporated) | 1.5 |
| Melamine resin (Trademark "Super Beckamine G-821" made by Dainippon Ink & Chemicals, Incorporated) | 1 |
| Titanium dioxide (Trademark "Tipaque CR-EL" made by Ishihara Sangyo Kaisha, Ltd.) | 5 |
| 2-butanone | 22.5 |

The thus prepared intermediate layer coating liquid was coated on an aluminum plate serving as an electroconductive support, and dried at 130° C. for 20 minutes. Thus, an intermediate layer with a thickness of about 4 μm was formed on the aluminum plate.

(Formation of charge generation layer)

3 parts by weight of the mixture of titanyltetraazaporphyrin compounds (mixture No. 1) prepared in Example 1—1, serving as a charge generation material, 2 parts by weight of a commercially available polyvinyl butyral resin (Trademark "BM-S", made by Sekisui Chemical Co., Ltd.), and 495 parts by weight of tetrahydrofuran were mixed and dispersed, and the mixture was subjected to ball milling in a ball mill using 2-mm diameter PSZ balls for 3 hours.

Thus, a coating liquid for charge generation layer was prepared.

The thus prepared charge generation layer coating liquid was coated on the above prepared intermediate layer, and dried at 100° C. for 20 minutes. Thus, a charge generation layer with a thickness of about 0.3 μm was provided on the intermediate layer.

(Formation of charge transport layer)

A mixture of 7 parts by weight of a charge transport material represented by formula (V) shown below, 10 parts by weight of a commercially available polycarbonate resin (Trademark "PCX-5" made by Teijin Chemicals Ltd.), and 0.0002 parts by weight of a commercially available silicone oil (Trademark "KFS0", made by Shin-Etsu Chemical Co., Ltd.) was dissolved in 83 parts by weight of dichloromethane, so that a coating liquid for charge transport layer was prepared.

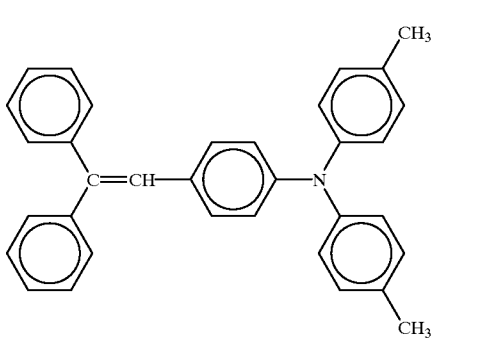

(V)

The thus prepared charge transport layer coating liquid was coated on the above prepared charge generation layer, and then dried at 110° C. for 20 minutes, so that a charge transport layer with a thickness of about 28 μm was provided on the charge generation layer.

Thus, an electrophotographic photoconductor No. 1 according to the present invention was fabricated.

The electrostatic characteristics of the thus fabricated photoconductor No. 1 were evaluated using a commercially available electrostatic copying sheet testing apparatus "Eaper Analyzer Model EPA-8100" (Trademark), made by Kawaguchi Electro Works Co., Ltd. The evaluation was carried out in a dynamic mode (at a rotational speed of 1000 rpm).

The electrophotographic photoconductor No. 1 according to the present invention was negatively charged in the dark under application of −6 kV for 20 seconds. Then, the photoconductor was allowed to stand in the dark for 20 seconds without applying any charge thereto, and the surface potential Vo (V) of the photoconductor was measured.

When the surface potential of the photoconductor No. 1 reached −800 V, the photoconductor was illuminated by white light of a halogen lamp in such a manner that the illuminance on the illuminated surface of the photoconductor was 5.3 lux. The exposure $Ew_{1/2}$ (lux·sec) required to reduce the surface potential (−800 V) to ½ the surface potential (−400 V) was measured.

Using the same electrostatic copying sheet testing apparatus as mentioned above, the photoconductor No. 1 was illuminated by monochromatic light of 780 nm in such a manner that the intensity of light on the illuminated surface of the photoconductor was 1 $\mu W/cm^2$. The exposure $Em_{1/2}$ ($\mu J/cm^2$) required to reduce the surface potential (−800 V) to ½ the surface potential (−400 V) was measured for evaluating the sensitivity with respect to the wave range of the LD, that is, the near infrared region.

The results are shown in TABLE 5.

Furthermore, the electrophotographic photoconductors were fabricated in the same manner as mentioned above, using as the charge generation materials the ten kinds of mixtures of titanyltetraazaporphyrin compounds which had been prepared in Example 1—1 in order to confirm the reproducibility of the preparation method.

When the electrostatic characteristics of the thus fabricated electrophotographic photoconductors were evaluated in the same manner as mentioned above, it was confirmed that the reproducibility was excellent with respect to the electrophotographic properties.

EXAMPLES 2—2 TO 2-19

The procedure for fabrication of the electrophotographic photoconductor No. 1 according to the present invention in Example 2-1 was repeated except that the mixture No. 1 serving as the charge generation material employed in Example 2-1 was replaced by the mixtures No. 2 to No. 19.

Thus, electrophotographic photoconductors No. 2 to No. 19 according to the present invention were fabricated.

The electrostatic characteristics of those photoconductors were evaluated in the same manner as in Example 2-1. The results are shown in TABLE 5.

EXAMPLE 2-20
[Fabrication of Layered Photoconductor]
(Formation of charge transport layer)

The same charge transport layer coating liquid as employed in Example 2-1 was coated on an aluminum-deposited polyester film by blade coating, and dried at 120° C. for 10 minutes, so that a charge transport layer with a thickness of about 20 μm was formed on the aluminum-deposited polyester film.

(Formation of charge generation layer)

A mixture of 13.5 parts by weight of the mixture No. 15 (a mixture of titanyltetraazaporphyrin compounds prepared in Example 1-15), 5.4 parts by weight of a commercially available polyvinyl butyral resin (Trademark "XYHL", made by Union Carbide Japan K.K.), 680 parts by weight of tetrahydrofuran, and 1020 parts by weight of ethyl cellosolve was pulverized and dispersed in a ball mill. With the addition of 1700 parts by weight of ethyl cellosolve to the above mixture, a coating liquid for charge generation layer was prepared.

The charge generation layer coating liquid was coated on the above prepared charge transport layer by spray coating, and dried at 100° C. for 10 minutes. Thus, a charge generation layer with a thickness of about 0.2 μm was formed on the charge transport layer.

(Formation of protective layer)

A commercially available polyamide resin (Trademark "CM-8000" made by Toray Industries, Inc.) was dissolved in a mixed solvent of methanol and n-butanol, so that a coating liquid for protective layer was prepared.

The protective layer coating liquid was coated on the above prepared charge generation layer by spray coating, and dried at 120° C. for 30 minutes, so that a protective layer with a thickness of about 0.5 μm was formed on the charge generation layer.

Thus, an electrophotographic photoconductor No. 20 according to the present invention was fabricated.

The electrostatic characteristics of the photoconductor No. 20 were evaluated in the same manner as in Example 2-1 except that the photoconductor was positively charged in the dark under application of +6 kV.

The results are shown in TABLE 5.

EXAMPLE 2-21
[Fabrication of Single-layered Photoconductor]

158 parts by weight of methyl ethyl ketone were added to one part by weight of the mixture No. 12 (mixture of titanyltetraazaporphyrin compounds prepared in Example 1-12), and the thus obtained mixture was subjected to ball milling for 24 hours using alumina balls with a diameter of 5 mm.

To this mixture, 12 parts by weight of the electron transport material of the following formula (S) and 18 parts by weight of a commercially available polyester resin (Trademark "Polyester Adhesive 49000" made by Du Pont Kabushiki Kaisha) were added. The thus prepared mixture was further dispersed, so that a coating liquid for photoconductive layer was prepared.

(S)

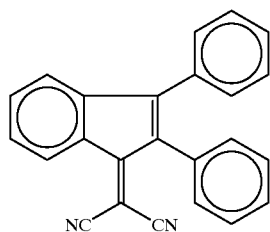

The photoconductive layer coating liquid was coated on an aluminum-deposited polyester film by a doctor blade, and dried at 100° C. for 30 minutes, whereby a photoconductive layer with a thickness of about 15 µm was formed on the aluminum-deposited polyester film.

Thus, an electrophotographic photoconductor No. 21 according to the present invention was fabricated.

The electrostatic characteristics of the photoconductor No. 21 were evaluated in the same manner as in Example 2-1 except that the photoconductor was positively charged in the dark under application of +6 kV.

The results are shown in TABLE 5.

COMPARATIVE EXAMPLE 2-1
[Fabrication of Comparative Layered Photoconductor]

The procedure for fabrication of the electrophotographic photoconductor No. 1 according to the present invention in Example 2-1 was repeated except that the mixture No. 1 serving as the charge generation material in Example 2-1 was replaced by the comparative compound No. 1 prepared in Comparative Example 1—1.

Thus, a comparative electrophotographic photoconductor No. 1 was fabricated.

The electrostatic characteristics of the comparative photoconductor No. 1 were evaluated in the same manner as in Example 1—1. The results are shown in TABLE 5.

COMPARATIVE EXAMPLE 2—2
[Fabrication of Comparative Layered Photoconductor]

The procedure for fabrication of the electraphotographic photoconductor No. 1 according to the present invention in Example 2-1 was repeated except that the mixture No. 1 serving as the charge generation material, in Example 2-1 was replaced by the comparative compound No. 2 prepared in Comparative Example 1-2.

Thus, a comparative electrophotographic photoconductor No. 2 was fabricated.

The electrostatic characteristics of the comparative photoconductor No. 2 were evaluated in the same manner as in Example 2-1. The results are shown in TABLE 5.

TABLE 5

| | Photoconductor No. | Mixture No. | Vo (V) | $Ew_{1/2}$ (lux · sec) | $Em_{1/2}$ (µJ/cm$^2$) |
|---|---|---|---|---|---|
| Ex. 2-1 | 1 | 1 | −743 | 0.77 | 0.41 |
| Ex. 2-2 | 2 | 2 | −832 | 0.64 | 0.33 |
| Ex. 2-3 | 3 | 3 | −780 | 0.74 | 0.38 |
| Ex. 2-4 | 4 | 4 | −734 | 0.76 | 0.39 |
| Ex. 2-5 | 5 | 5 | −838 | 0.84 | 0.47 |

TABLE 5-continued

| | Photoconductor No. | Mixture No. | Vo (V) | $Ew_{1/2}$ (lux · sec) | $Em_{1/2}$ (µJ/cm$^2$) |
|---|---|---|---|---|---|
| Ex. 2-6 | 6 | 6 | −825 | 0.78 | 0.43 |
| Ex. 2-7 | 7 | 7 | −815 | 0.91 | 0.55 |
| Ex. 2-8 | 8 | 8 | −1034 | 0.19 | 0.12 |
| Ex. 2-9 | 9 | 9 | −1093 | 0.17 | 0.10 |
| Ex. 2-10 | 10 | 10 | −1134 | 0.17 | 0.10 |
| Ex. 2-11 | 11 | 11 | −1024 | 0.21 | 0.14 |
| Ex. 2-12 | 12 | 12 | −996 | 0.21 | 0.16 |
| Ex. 2-13 | 13 | 13 | −914 | 0.27 | 0.18 |
| Ex. 2-14 | 14 | 14 | −616 | 0.50 | 0.31 |
| Ex. 2-15 | 15 | 15 | −947 | 0.43 | 0.21 |
| Ex. 2-16 | 16 | 16 | −1242 | 0.22 | 0.15 |
| Ex. 2-17 | 17 | 17 | −1013 | 0.27 | 0.19 |
| Ex. 2-18 | 18 | 18 | −798 | 0.31 | 0.15 |
| Ex. 2-19 | 19 | 19 | −963 | 0.23 | 0.15 |
| Ex. 2-20 | 20 | 15 | +1122 | 0.31 | 0.25 |
| Ex. 2-21 | 21 | 12 | +826 | 0.36 | 0.29 |
| Comp. Ex. 2-1 | Comparative Photoconductor No. 1 | Comparative Compound No. 1 | −567 | 4.50 | 2.26 |
| Comp. Ex. 2-2 | Comparative Photoconductor No. 2 | Comparative Compound No. 2 | −655 | 2.12 | 1.55 |

COMPARATIVE EXAMPLE 2-3
[Fabrication of Comparative Layered Photoconductor]

Figure 7:
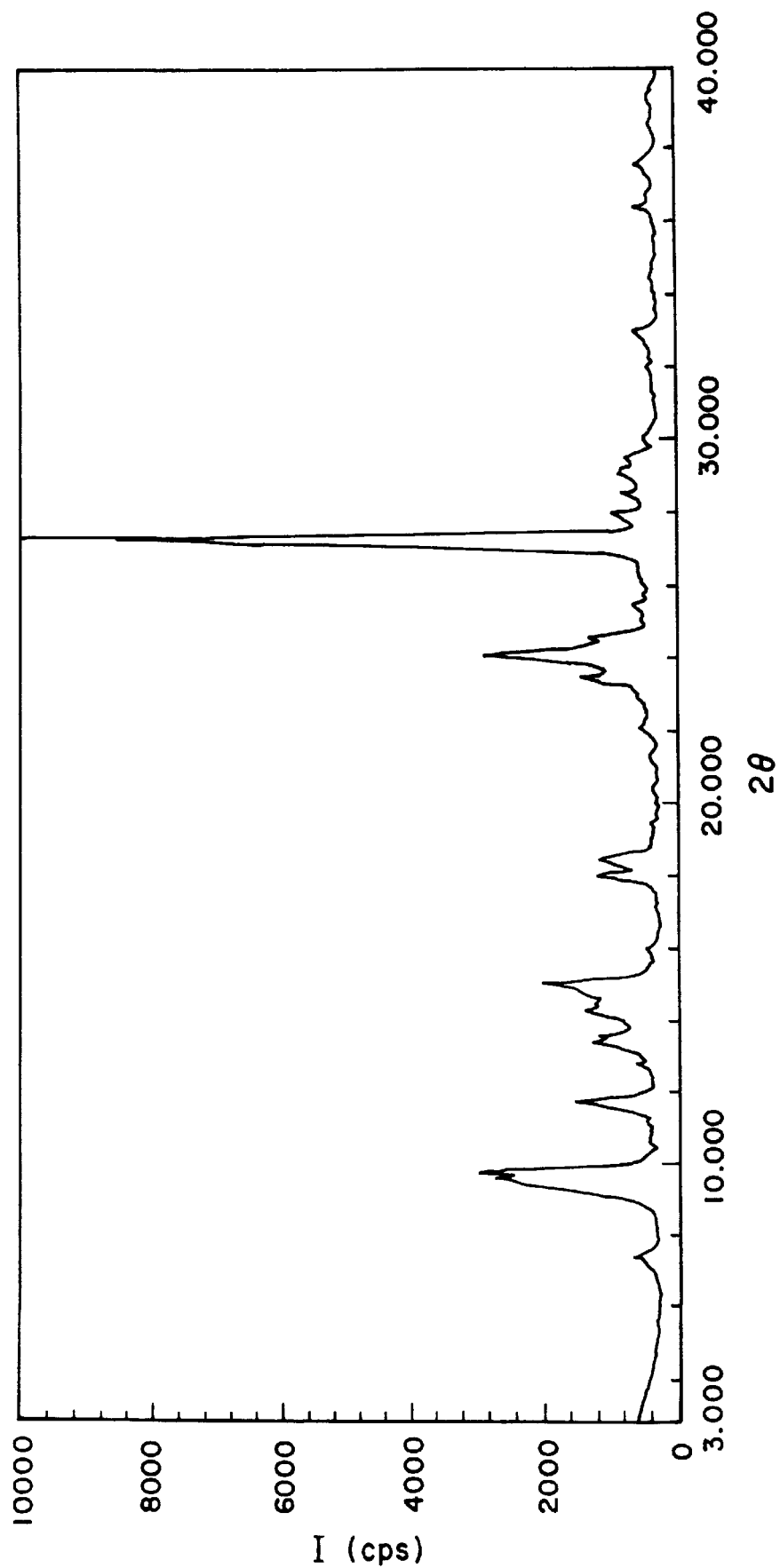
FIG. 7 is an X-ray diffraction spectrum of a Y-type titanylphthalocyanine in the form of a powder employed in an electrophotographic photoconductor fabricated in Comparative Example 2-3.

The procedure for fabrication of the electrophotographic photoconductor No. 1 according to the present invention in Example 2-1 was repeated except that the mixture No. 1 serving as the charge generation material in Example 2-1 was replaced by such a Y-type titanylphthalocyanine compound that exhibited an X-ray diffraction spectrum shown in FIG. 7.

Thus, a comparative electrophotographic photoconductor No. 3 was fabricated.

The electrostatic fatigue characteristics of the comparative photoconductor No. 3 were evaluated using a commercially available electrostatic copying sheet testing apparatus "Paper Analyzer Model EPA-8100" (Trademark), made by Kawaguchi Electro Works Co., Ltd. The evaluation was carried out in a dynamic mode (at a rotational speed of 1000 rpm).

The comparative electrophotographic photoconductor No. 3 was negatively charged in the dark under application of −6 kV, while exposed to white light of a halogen lamp, with the conduction current being maintained at about 5.6 µA, and the charging potential at −800 V. 30 minutes later, the surface potential was measured. Upon measurement, the photoconductor was again charged while exposed to light for 30 minutes in the same manner as mentioned above. Then, the surface potential was again measured.

The photoconductor No. 1 according to the present invention fabricated in Example 2-1 was also subjected to the above-mentioned fatigue test to evaluate the electrostatic fatigue characteristics.

Figure 8:
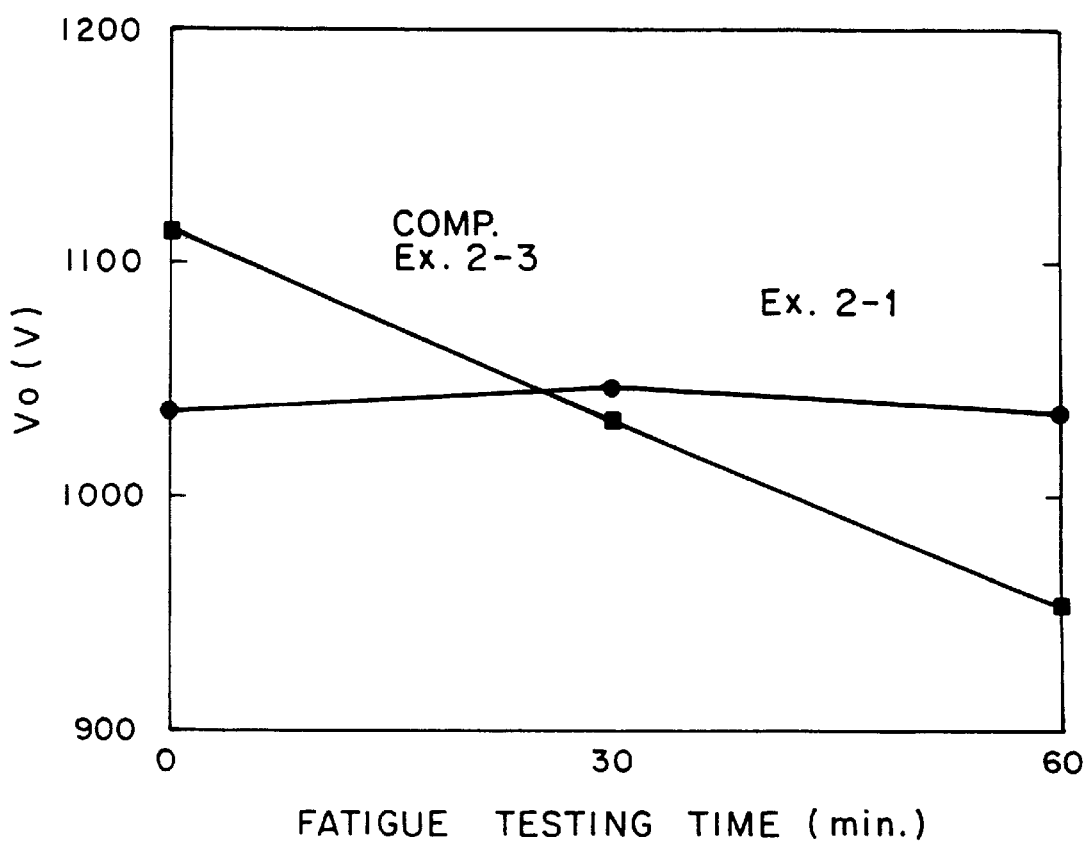
FIG. 8 is a chart showing the change in surface potential of the electrophotographic photoconductors obtained in Example 2-1 and Comparative Example 2-3 in the fatigue test.

FIG. 8 shows the change in surface potential (V) of each photoconductor in the above-mentioned fatigue test.

As can be seen from the results shown in FIG. 8, the surface potential of the photoconductor No. 1 was more stable than that of the comparative photoconductor No. 3 in the fatigue test. The mixture of a plurality of different titanyltetraazaporphyrin compounds serving as the photoconductive material in the photoconductor is considered to be useful to stabilize the electrostatic characteristics in the fatigue performance.

COMPARATIVE EXAMPLE 2-4
[Fabrication of Comparative Layered Photoconductor]

The procedure for fabrication of the electrophotographic photoconductor No. 1 according to the present invention in Example 2-1 was repeated except that the mixture No. 1 serving as the charge generation material in Example 2-1 was replaced by the comparative compound No. 3 prepared in Comparative Example 1-3.

Thus, a comparative electrophotographic photoconductor No. 4 was fabricated.

The electrostatic characteristics of the comparative photoconductor No. 4 were evaluated in the same manner as in Example 2-1. As a result, the surface potential (Vo) was −585 V. In addition, there were no sensitivities to both the white light and the monochromatic light when the comparative compound No. 3 was employed in the photoconductor.

EXAMPLE 3-1

[Fabrication of Image Forming Apparatus]

An image forming apparatus was provided with the electrophotographic photoconductor No. 1 (fabricated in Example 2-1) according to the present invention.

Using the above-mentioned image forming apparatus, images were produced. The produced images were remarkably clear.

As previously explained, the mixture of a plurality of different titanyltetraazaporphyrin compounds according to the present invention is useful as the organic photoconductive material for the electrophotographic photoconductor which is employed in the high-speed copying machine or laser printer.

The photoconductor of the present invention is superior to the conventional photoconductor because the sensitivity is excellent not only in the visible light range, but also in the near infrared range, the charging characteristics are improved, and the fatigue properties are also excellent. Therefore, the photoconductor of the present invention is considered to be useful when employed in the high-speed copying machine and laser printer.

Japanese Patent Application No. 10-328248 filed Nov. 18, 1998 is hereby incorporated by reference.

What is claim is:

1. An electrophotographic photoconductor which comprises an electroconductive support and a photoconductive layer formed thereon comprising a mixture of a plurality of different titanyltetraazaporphyrin compounds, each of which is represented by formula (1):

(1)

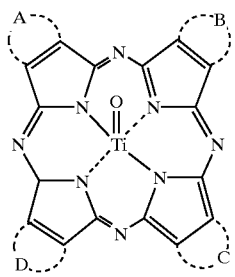

wherein A, B, C and D are each independently an unsubstituted benzene ring or an unsubstituted pyridine ring.

2. The photoconductor as claimed in claim 1, wherein said mixture exhibits at least one of diffraction peaks at 6.9°, 26.2°, 27.2° and 28.5° in terms of a Bragg angle of $2\theta \pm 0.2°$ in an X-ray diffraction spectrum using a Cu-Kα ray with a wavelength of 1.54 Å.

3. The photoconductor as claimed in claim 1, wherein said mixture of said titanyltetraazaporphyrin compounds is produced by allowing phthalonitrile, dicyanopyridine, and a titanium compound to react.

4. An image forming apparatus comprising an electrophotographic photoconductor which comprises an electroconductive support and a photoconductive layer formed thereon comprising a mixture of a plurality of different titanyltetraazaporphyrin compounds, each of which is represented by formula (1):

(1)

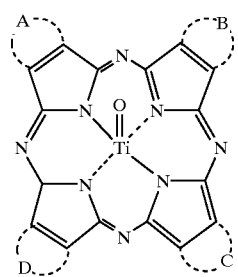

wherein A, B, C and D are each independently an unsubstituted benzene ring or an unsubstituted pyridine ring.

5. The photoconductor as claimed in claim 1, wherein the mixture of said titanyltetraazaporphyrin compounds is synthesized from phthalonitrile and dicyanopyridine, wherein a molar ratio of phthalonitrile to dicyanopyridine is in a range of 1:99999 to 99999:1.

6. The photoconductor as claimed in claim 5, wherein the mixture of said titanyltetraazaporphyrin compounds is synthesized from phthalonitrile and dicyanopyridine, wherein a molar ratio of phthalonitrile to dicyanopyridine is in a range of 1:1 to 399:1.

7. The photoconductor as claimed in claim 3, wherein said dicyanopyridine is 2,3-dicyanopyridine or 3,4-dicyanopyridine.

8. The photoconductor as claimed in claim 3, wherein said titanium compound is titanium tetrachloride or tetra-n-butyl-o-titanate.

9. The photoconductor as claimed in claim 7, wherein said dicyanopyridine is substituted with a group selected from the group consisting of a nitro group, a cyano group, a halogen atom, an alkyl group having 1 to 8 carbon atom, an alkoxyl group having 1 to 8 carbon atoms, and an aryl group.

* * * * *

UNITED STATES PATENT AND TRADEMARK OFFICE
CERTIFICATE OF CORRECTION

PATENT NO. : 6,524,761 B2
DATED : February 25, 2003
INVENTOR(S) : Tomoyuki Shimada et al.

It is certified that error appears in the above-identified patent and that said Letters Patent is hereby corrected as shown below:

Column 2,
Line 4, "The wave range of the currently used Lo is within the near" should read -- The wave range of the currently used LD is within the near --.

Column 3,
Line 44, "577, 579, 579 and 580" should read -- 577, 578, 579 and 580 --.

Column 10,
Line 59, "Application S3-132347)," should read -- Application 53-132347), --.

Column 12,
Line 66, "include a positive hole" should read -- includes a positive hole --.

Column 14,
Lines 29-30, "1,1-bis(4-dibenzylaminophenyl)propane" should read -- 1,1-bis(4-dibenzylaminophenyl) propane --.

Column 15,
Line 17, ", an. alkyl group" should read -- , an alkyl group --.

Column 17,
Line 25, "and n igs an integer" should read -- and n is an integer --.

Column 24,
Line 45, "metioned sulfuric acid" should read -- mentioned sulfuric acid --.

Column 25,
Line 30, "$C_{28}H_{12}N_{12}OTi$: 580.37 m/z  ②" should read -- $C_{28}H_{12}N_{12}OTi$: 580.37 m/z  ① --.

Column 27,
Line 31, "Eaper Analyzer Model EPA-8100" should read -- Paper Analyzer Model EPA-8100 --.

UNITED STATES PATENT AND TRADEMARK OFFICE
CERTIFICATE OF CORRECTION

PATENT NO. : 6,524,761 B2
DATED : February 25, 2003
INVENTOR(S) : Tomoyuki Shimada et al.

It is certified that error appears in the above-identified patent and that said Letters Patent is hereby corrected as shown below:

Column 31,
Line 40, "What is claim is" should read -- What is claimed is --.

Column 32,
Line 56, "carbon atom" should read -- carbon atoms --.

Signed and Sealed this

Seventh Day of October, 2003

JAMES E. ROGAN
*Director of the United States Patent and Trademark Office*